(12) United States Patent
Millard

(10) Patent No.: US 10,343,964 B2
(45) Date of Patent: Jul. 9, 2019

(54) PROCESSES FOR FORMING TITANIUM CATECHOL COMPLEXES

(71) Applicant: LOCKHEED MARTIN ADVANCED ENERGY STORAGE, LLC, Bethesda, MD (US)

(72) Inventor: Matthew Millard, Cambridge, MA (US)

(73) Assignee: Lockheed Martin Energy, LLC, Bethesda, MD (US)

( * ) Notice: Subject to any disclaimer, the term of this patent is extended or adjusted under 35 U.S.C. 154(b) by 225 days.

(21) Appl. No.: 15/220,322

(22) Filed: Jul. 26, 2016

(65) Prior Publication Data
US 2018/0029965 A1 Feb. 1, 2018

(51) Int. Cl.
C07C 37/66 (2006.01)
C07C 303/22 (2006.01)
(Continued)

(52) U.S. Cl.
CPC ............ *C07C 37/66* (2013.01); *C07C 303/22* (2013.01); *H01M 8/08* (2013.01); *H01M 8/083* (2013.01); *H01M 2300/0002* (2013.01)

(58) Field of Classification Search
CPC ............ C07C 37/66; C07C 3/22; H01M 8/08; H01M 8/083
See application file for complete search history.

(56) References Cited

U.S. PATENT DOCUMENTS 1,279,295 A 9/1918 Downs
2,353,782 A 7/1944 Neumark
(Continued)

FOREIGN PATENT DOCUMENTS

CN 1284208 A 2/2001
CN 101877412 A 11/2010
(Continued)

OTHER PUBLICATIONS

Abdulghani et al., "Preparation and Characterization of Di-, Tri-, and Tetranuclear Schiff Base Complexes Derived from Diamines and 3,4-Dihydroxybenzaldehyde," Hindawi Publishing Corp, Bioinorganic Chemistry and Applications, 2013, pp. 1-14.
(Continued)

*Primary Examiner* — Helen Oi K Conley
(74) *Attorney, Agent, or Firm* — BakerHostetler

(57) ABSTRACT

Titanium complexes containing catecholate ligands can be desirable active materials for flow batteries and other electrochemical energy storage systems. Such complexes can be formed, potentially on very large scales, through reacting a catechol compound in an organic solvent with titanium tetrachloride, and then obtaining an aqueous phase containing an alkali metal salt form of the titanium catechol complex. More specifically, the methods can include: forming a catechol solution and heating, adding titanium tetrachloride to the catechol solution, reacting the titanium tetrachloride with a catechol compound to evolve HCl gas and to form an intermediate titanium catechol complex, and adding an alkaline aqueous solution to the intermediate titanium catechol complex to form an alkali metal salt form titanium catechol complex that is at least partially dissolved in an aqueous phase. The aqueous phase can be separated from an organic phase. The resulting complexes can be substantially free of alkali metal halide salts.

25 Claims, 6 Drawing Sheets

(51) Int. Cl.
*H01M 8/08* (2016.01)
*H01M 8/083* (2016.01)

(56) References Cited

U.S. PATENT DOCUMENTS

| | | |
|---|---|---|
| 2,415,792 A | 2/1947 | Gravell |
| 3,294,588 A | 12/1966 | Morton |
| 3,425,796 A | 2/1969 | Bauer |
| 3,428,654 A | 2/1969 | Rubinfeld |
| 3,573,984 A | 4/1971 | Shah |
| 3,707,449 A | 12/1972 | Reinhardt et al. |
| 3,772,379 A | 11/1973 | Woodgate |
| 3,801,642 A | 4/1974 | Worrel |
| 3,876,435 A | 4/1975 | Dollman |
| 3,916,004 A | 10/1975 | Okada et al. |
| 3,919,000 A | 11/1975 | Yarrington |
| 3,920,756 A | 11/1975 | Tahara et al. |
| 3,929,506 A | 12/1975 | Leddy et al. |
| 3,985,517 A | 10/1976 | Johnson |
| 3,985,585 A | 10/1976 | Tuttle et al. |
| 4,046,861 A | 9/1977 | Reinhardt et al. |
| 4,064,324 A | 12/1977 | Eustace |
| 4,069,371 A | 1/1978 | Zito |
| 4,126,529 A | 11/1978 | DeBerry |
| 4,180,623 A | 12/1979 | Adams |
| 4,202,799 A | 5/1980 | Yoshimura et al. |
| 4,233,144 A | 11/1980 | Pace et al. |
| 4,362,791 A | 12/1982 | Kaneko et al. |
| 4,378,995 A | 4/1983 | Gratzfeld et al. |
| 4,410,606 A | 10/1983 | Loutfy et al. |
| 4,436,711 A | 3/1984 | Olson |
| 4,436,712 A | 3/1984 | Olson |
| 4,436,713 A | 3/1984 | Olson |
| 4,436,714 A | 3/1984 | Olson |
| 4,443,423 A | 4/1984 | Olson |
| 4,443,424 A | 4/1984 | Olson |
| 4,468,441 A | 8/1984 | D'Agostino et al. |
| 4,485,154 A | 11/1984 | Remick et al. |
| 4,520,083 A | 5/1985 | Prater et al. |
| 4,563,403 A | 1/1986 | Julian |
| 4,592,973 A | 6/1986 | Pemsler et al. |
| 4,617,244 A | 10/1986 | Greene |
| 4,680,308 A | 7/1987 | Schwartz et al. |
| 4,818,646 A | 4/1989 | Takakubo et al. |
| 4,880,758 A | 11/1989 | Heistand, II et al. |
| 4,952,289 A | 8/1990 | Ciccone et al. |
| 4,959,135 A | 9/1990 | Zenner et al. |
| 4,973,720 A | 11/1990 | Saito et al. |
| 5,084,533 A | 1/1992 | Shah et al. |
| 5,102,906 A | 4/1992 | Nakayama et al. |
| 5,122,461 A | 6/1992 | Hsiung et al. |
| 5,264,097 A | 11/1993 | Vaughan |
| 5,302,481 A | 4/1994 | Ong |
| 5,318,865 A | 6/1994 | Kaneko et al. |
| 5,433,934 A | 7/1995 | Chang et al. |
| 5,472,807 A | 12/1995 | Licht et al. |
| 5,643,670 A | 7/1997 | Chung |
| 5,679,239 A | 10/1997 | Blum et al. |
| 5,759,711 A | 6/1998 | Miyabayashi et al. |
| 5,785,841 A | 7/1998 | Tseng |
| 5,876,581 A | 3/1999 | Itaya et al. |
| 5,910,366 A | 6/1999 | Chowdhury et al. |
| 6,001,326 A | 12/1999 | Kim et al. |
| 6,030,517 A | 2/2000 | Lincot et al. |
| 6,054,230 A | 4/2000 | Kato |
| 6,461,772 B1 | 10/2002 | Miyake et al. |
| 6,475,661 B1 | 11/2002 | Pellegri et al. |
| 6,485,868 B1 | 11/2002 | Tsujioka et al. |
| 6,555,989 B1 | 4/2003 | Pearson |
| 6,585,951 B1 | 7/2003 | Hong et al. |
| 6,624,328 B1 | 9/2003 | Guerra |
| 7,046,418 B2 | 5/2006 | Lin et al. |
| 7,193,764 B2 | 3/2007 | Lin et al. |
| 7,223,833 B1 | 5/2007 | Nielsen et al. |
| 7,252,905 B2 | 8/2007 | Clarke et al. |
| 7,265,162 B2 | 9/2007 | Yandrasits et al. |
| 7,348,088 B2 | 3/2008 | Hamrock et al. |
| 7,463,917 B2 | 12/2008 | Martinez |
| 7,508,568 B2 | 3/2009 | Lin et al. |
| 7,550,231 B2 | 6/2009 | Stauffer |
| 7,557,164 B2 | 7/2009 | Felix et al. |
| 7,625,663 B2 | 12/2009 | Clarke et al. |
| 7,645,540 B2 | 1/2010 | Boone et al. |
| 7,678,728 B2 | 3/2010 | Olson et al. |
| 7,745,056 B2 | 6/2010 | Lee et al. |
| 7,767,777 B2 | 8/2010 | Buesing et al. |
| 7,927,731 B2 | 4/2011 | Sahu |
| 7,931,981 B2 | 4/2011 | Boone et al. |
| 7,935,366 B2 | 5/2011 | Pahuja et al. |
| 7,998,335 B2 | 8/2011 | Feeney et al. |
| 8,129,554 B2 | 3/2012 | Schwaiger |
| 8,187,441 B2 | 5/2012 | Evans et al. |
| 8,445,118 B2 | 5/2013 | Cordonier et al. |
| 8,492,581 B2 | 7/2013 | Frost |
| 8,691,413 B2 | 4/2014 | Esswein et al. |
| 8,753,761 B2 | 6/2014 | Esswein et al. |
| 9,300,000 B2 | 3/2016 | Jansen et al. |
| 9,382,274 B2 | 7/2016 | Esswein et al. |
| 9,409,842 B1 | 8/2016 | Fu et al. |
| 2002/0177042 A1 | 11/2002 | Amendola |
| 2003/0068561 A1 | 4/2003 | Okahara et al. |
| 2003/0143456 A1 | 7/2003 | Kazacos et al. |
| 2003/0228394 A1 | 12/2003 | Abdel-Monem et al. |
| 2004/0096746 A1 | 5/2004 | Wietelmann et al. |
| 2005/0098437 A1 | 5/2005 | Shiepe |
| 2005/0244707 A1 | 11/2005 | Skyllas-Kazacos et al. |
| 2006/0047094 A1 | 3/2006 | Cherkasov et al. |
| 2007/0275291 A1 | 11/2007 | Gu et al. |
| 2008/0274385 A1 | 11/2008 | Creeth |
| 2008/0292964 A1 | 11/2008 | Kazacos et al. |
| 2009/0110998 A1 | 4/2009 | Miyachi et al. |
| 2009/0130525 A1 | 5/2009 | Miyachi et al. |
| 2009/0208807 A1 | 8/2009 | Miyachi et al. |
| 2009/0308752 A1 | 12/2009 | Evans et al. |
| 2010/0003586 A1 | 1/2010 | Sahu |
| 2010/0059388 A1 | 3/2010 | Clarke et al. |
| 2010/0086823 A1 | 4/2010 | Koshino et al. |
| 2010/0086983 A1 | 4/2010 | Gellett et al. |
| 2010/0239946 A1 | 9/2010 | Miyachi et al. |
| 2011/0014532 A1 | 1/2011 | Knuckey et al. |
| 2011/0136016 A1 | 6/2011 | Huang et al. |
| 2011/0189549 A1 | 8/2011 | Sun et al. |
| 2011/0195283 A1 | 8/2011 | Sun et al. |
| 2011/0200890 A1 | 8/2011 | Kocherginsky |
| 2011/0223450 A1 | 9/2011 | Horne et al. |
| 2011/0244277 A1 | 10/2011 | Gordon, II et al. |
| 2011/0244367 A1 | 10/2011 | Watahiki et al. |
| 2012/0052347 A1 | 3/2012 | Wilson et al. |
| 2012/0077095 A1 | 3/2012 | Roumi et al. |
| 2012/0107661 A1 | 5/2012 | Lee et al. |
| 2012/0135278 A1 | 5/2012 | Yoshie et al. |
| 2012/0171541 A1 | 7/2012 | Park et al. |
| 2012/0183868 A1 | 7/2012 | Toussaint et al. |
| 2012/0196188 A1 | 8/2012 | Zhang et al. |
| 2012/0202099 A1 | 8/2012 | Perry et al. |
| 2012/0208061 A1 | 8/2012 | Sahu et al. |
| 2012/0244406 A1 | 9/2012 | Xia et al. |
| 2012/0263990 A1 | 10/2012 | Kim |
| 2013/0004819 A1 | 1/2013 | Mun et al. |
| 2013/0157087 A1 | 6/2013 | Pandy et al. |
| 2013/0252062 A1 | 9/2013 | Wilkins et al. |
| 2013/0252137 A1 | 9/2013 | Zhang et al. |
| 2014/0028260 A1 | 1/2014 | Goeltz et al. |
| 2014/0028261 A1 | 1/2014 | Esswein et al. |
| 2014/0030572 A1 | 1/2014 | Esswein et al. |
| 2014/0030573 A1 | 1/2014 | Esswein et al. |
| 2014/0030631 A1 | 1/2014 | Esswein et al. |
| 2014/0051003 A1 | 2/2014 | Esswein et al. |
| 2014/0080035 A1 | 3/2014 | Esswein et al. |
| 2014/0138576 A1 | 5/2014 | Esswein et al. |
| 2014/0178735 A1 | 6/2014 | Wang et al. |
| 2014/0193687 A1 | 7/2014 | Park et al. |
| 2014/0239906 A1 | 8/2014 | Anderson et al. |
| 2014/0274936 A1 | 9/2014 | Piccariello et al. |

(56) References Cited

U.S. PATENT DOCUMENTS

| | | |
|---|---|---|
| 2014/0349177 A1 | 11/2014 | Chung et al. |
| 2014/0377666 A1 | 12/2014 | Kodama et al. |
| 2015/0236543 A1 | 8/2015 | Brushett et al. |
| 2015/0372333 A1 | 12/2015 | Odom et al. |
| 2016/0066578 A1 | 3/2016 | Ala'Aldeen et al. |
| 2016/0149251 A1 | 5/2016 | Reece |
| 2016/0208165 A1 | 7/2016 | Li et al. |
| 2016/0264603 A1 | 9/2016 | Esswein et al. |
| 2016/0268623 A1 | 9/2016 | Esswein et al. |
| 2016/0272659 A1 | 9/2016 | King et al. |
| 2016/0276693 A1 | 9/2016 | Goeltz et al. |
| 2016/0276694 A1 | 9/2016 | Goeltz et al. |
| 2016/0276695 A1 | 9/2016 | Esswein et al. |
| 2017/0253620 A1 | 9/2017 | Humbarger et al. |
| 2017/0256811 A1 | 9/2017 | Humbarger et al. |
| 2017/0271704 A1 | 9/2017 | Morris-Cohen |

FOREIGN PATENT DOCUMENTS

| | | | |
|---|---|---|---|
| EP | 0814527 | A2 | 12/1997 |
| EP | 1290068 | A2 | 3/2003 |
| EP | 1411576 | A1 | 4/2004 |
| EP | 1901379 | A1 | 3/2008 |
| EP | 2235781 | A1 | 10/2010 |
| EP | 2463950 | A1 | 6/2012 |
| FR | 153366 | A | 7/1968 |
| GB | 1354886 | A | 6/1974 |
| WO | WO-95/12219 | A1 | 5/1995 |
| WO | WO-1997/017354 | A1 | 5/1997 |
| WO | WO-2004/095602 | A2 | 11/2004 |
| WO | WO-2006/135958 | A1 | 12/2006 |
| WO | WO-2007/044852 | A2 | 4/2007 |
| WO | WO-2007/101284 | A1 | 9/2007 |
| WO | WO-2011/075135 | A1 | 6/2011 |
| WO | WO-2011/098781 | A1 | 8/2011 |
| WO | WO-2011/149624 | A1 | 12/2011 |
| WO | WO-2012/075810 | A1 | 6/2012 |
| WO | WO-2013/006427 | A1 | 1/2013 |
| WO | WO-2013/048603 | A1 | 4/2013 |
| WO | WO 2014-018593 | A1 | 1/2014 |
| WO | WO-2015/069439 | A1 | 5/2015 |

OTHER PUBLICATIONS

IUPAC Compendium of Chemical Terminology, "coordinatively unsaturated complex," 1997, http://old.iupac.org/goldbook/C01334.pdf.

Mansoor, "Mixed Metal Complexes of Copper (II), Nickel (II) and Zinc (II) Involving Dopa and Dopamine," International Journal of ChemTech Research, Jan.-Mar. 2010, vol. 2, No. 1, pp. 640-645.

International Search Report and Written Opinion from PCT/US17/14764, dated Apr. 20, 2017.

International Search Report and Written Opinion from PCT/US16/69190, dated May 3, 2017.

International Search Report and Written Opinion from PCT/US2017/022203, dated Jun. 6, 2017.

Ali et al., "Synthesis and Processing Characteristics of $Ba_{0.65}Sr_{0.35}TiO_3$ Powders from Catecholate Precursors," J Am Ceram Soc, 1993, pp. 2321-2326, vol. 76, No. 9.

Devi et al., "pH-metric investigation on Mixed-Ligand Complexes of Ca(II), Mg(II) and Zn(II) with L-Dopa and 1,10 Phenantroline in Propylene glycol-Water Mixtures," RRJC, Oct.-Dec. 2012, vol. 1, Issue 1, pp. 13-22.

Xu, "Mechanics of metal-catecholate complexes: The roles of coordination state and metal types," Scientific Reports, Oct. 10, 2013, 3:2914, pp. 1-7.

Soloveichik, "Flow Batteries: Current Status and Trends," 2015, Chem. Rev., 115 (20), pp. 11533-11558.

Davies, "Electroceramics from Source Materials via Molecular Intermediates: $BaTlO_3$ from $TlO_2$ via $[Tl(catecholate)_3]^{2-}$," May 1990, J. Am. Ceram, Soc., Aug. 1990, 73(5), 1429-30.

Ahluwalia et al., Intermediates for Organic Synthesis, Chapter 1, Phenols, Sections 1.21 and 1.23, (2003), I.K. International Pvt. Ltd.

Vliet et al., "Hydroxyhydroquinone Triacetate," Organic Synthesys, 1941, Coll vol. 1, p. 317 (1941), vol. 4, p. 35 (1925) 3 pages.

International Search Report and Written Opinion dated Jan. 19, 2017 from International Application No. PCT/US16/58433.

International Search Report and Written Opinion dated Feb. 17, 2017 from International Application No. PCT/US16/65159.

Brezina, "Study of the reduction of oxygen on a carbon paste electrode in an alkaline medium," Coll. Czech. Chem. Commun., 1973, 38(10), 3024-3031.

Caulton, "Systematics and Future Projections Concerning Redox-Noninnocent Amide/Imine Ligands," Eur. J. Inorg. Chem., Jan. 2012, 2012(3), 435-443.

Cerofontain et al. "Sulfonation and sulfation on reaction of 1,2-dihydroxybenzene and its methyl ethers in concentrated aqueous sulfuric acid," Recl Tray Chim Pays-Bas, 1988, pp. 325-330, vol. 107.

Chen, "Solution Redox Couples for Electrochemical Energy Storage: I. Iron (III)-Iron (II) Complexes with O-Phenanthroline and Related Ligands," Journal of the Electrochemical Society, Jul. 1981, 128(7), 1460-1467.

Cohen, "The Association of Ferrocyanide Ions With Various Cations," J. Phys. Chem., Aug. 1957, 61(8), 1096-1100.

Davies, "Eiectroceramics from Source Materials via Molecular Intermediates: $PbTiO3$ from $TiO2$ via $[Ti(catecholate)3]2-$," J. Am. Ceram. Soc., Aug. 1990, 73(8), 2570-2572.

Dehaen et al, "A Self-Assembled Complex with a Titanium (IV) Catecholate Core as a Potential Bimodal Contrast Agent," Chem Eur J, 2012, pp. 293-302, vol. 18.

Fryda, "Wastewater Treatment With Diamond Electrodes," Diamond Materials, Electrochemical Society Proceedings, 2000, 99(32), 473-483.

Gail, "Cyano Compounds, Inorganic" in Ullmann's Encyclopedia of Industrial Chemistry, 2012, 10, 674-710.

Hollandsworth, "Zinc/Ferrocyanide Battery Development Phase IV" Lockheed Missiles and Space Company, Inc., Contractor report, Sandia Contract DE-AC04-76DP00789, May 1985, 278 pages.

Kim, "Novel catalytic effects of $Mn3O4$ for all vanadium redox flow batteries," Chem. Commun., Apr. 2012, 48(44), 5455-5457.

Kulesza, "Electrochemical preparation and characterization of hybrid films composed of Prussian blue type metal hexacyanoferrate and conducting polymer," Electrochimica Acta, Aug. 2001, 46(26-27), 4065-4073.

Leung, "Development of a Zinc-Cerium Redox Flow Battery", 2011, 352 pages.

Leung, "An undivided zinc-cerium redox flow battery operating at room temperature (295 K)," Electrochemistry Communications, 2011, vol. 13, pp. 770-773.

Leung, "Ce(III)/Ce(iV) in methanesulfonic acid as the positive half cell of a redox flow battery," Electrochimica Acta, 2011, vol. 56, pp. 2145-2153.

Leung, "Zinc deposition and dissolution in methanesulfonic acid onto a carbon composite electrode as the negative electrode reactions in a hybrid redox flow battery," Electrochimica Acta, 2011, vol. 56, pp. 6536-6546.

Leung, "Characterization of a zinc-cerium flow battery," Journal of Power Sources, 2011, vol. 195, pp. 5174-5185.

Modiba, "Electrochemical impedance spectroscopy study of Ce(IV) with aminopolycarboxylate ligands for redox flow batteries applications," Journal of Power Sources, May 2012, vol. 205, 1-9.

Modiba, "Electrochemical study of cerium(IV) in the presence of ethylenediaminetetraacetic acid (EDTA) and diethylenetriaminepentaacetate (DTPA) ligands," Journal of Applied Electrochemistry, Sep. 2008, 38(9), 1293-1299.

Modiba, "Electrolytes for redox flow battery systems," Dissertation presented for the degree of Doctor of Philosophy Chemistry at the University of Stellenbosch, Department of Chemistry and Polymer Science, Mar. 2010.

Nguyen, "Flow Batteries," The Electrochemical Society Interface, Fall2010, 19(3), 54-56.

(56) References Cited

OTHER PUBLICATIONS

Pharr, "Infrared Spectroelectrochemical Analysis of Adsorbed Hexacyanoferrate Species Formed during Potential Cycling in the Ferrocyanide/Ferricyanide Redox Couple," Anal. Chem., Nov. 1997, 69(22), 4673-4679.
Raymond, "Coordination isomers of biological iron transport compounds. VI. Models of the enterobactin coordination site. A crystal field effect in the structure of potassium tris( catecholato )chromate( III) and -ferrate( III) sesq u ihyd rates, K3[M( 02C6H4 )3]. 1 . 5H20, M=chromium, iron," J. Am. Chem. Soc., Mar. 1976, 98(7), 1767-1774.
Saito et al. "DPPH radical-scavenging reaction of protocatechuic acid: differnce in reactivity between acids and their esters," Hely Chim Acta, 2006, pp. 1395-1407, vol. 89.
Sever et al, "Visible absorption spectra of metal-catecholate and metal-tironate complexes," Dalton Trans., pp. 1061-1072, 2004.
Sigma-Aldrich Tris(hydroxymethyl)aminomethane, 2015.
Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4.
Steenken, "One-electron redox potentials of phenols. Hydroxy- and aminophenols and related compounds of biological interest," J. Phys. Chem., Sep. 1982, 86(18), 3661-3667.
Torres-Gomez, "Energy Storage in Hybrid Organic-Inorganic Materials Hexacyanoferrate-Doped Polypyrrole as Cathode in Reversible Lithium Cells," J. of the Electrochemical Society, 2000, 147(7), 2513-2516.
Trant, "Solubility of Sodium Ferrocyanide and Potassium Ferrocyanide in Solutions of NaOH and KOH Mixtures at 25.degree. C," University of Rochester, The David T. Kearns Center, Xerox Undergraduate Research Fellows Program, Jul. 28, 2011, 1 page.
Vercillo, "Solubility of Sodium Ferrocyanide in Sodium Hydroxide and Potassium Ferrocyanide in Potassium Hydroxide," University of Rochester, The David T. Kearns Center, Xerox Undergraduate Research Fellows Program, Jul. 28, 2011, 1 page.
Wang, "Determination of iron, titanium, osmium, and aluminum with tiron by reversephase high Performance liquid chromatography/ electrochemistry," Microchem. J., Jun. 1991, 43(3), 191-197.
Weber, "Redox flow batteries: a review," Journal of Applied Electrochemistry, Oct. 2011, 41(10), 1137-1164.
Murakami et al., "The Chelating Behavior of Catechol-4-sulfonate with Iron(III) Ion," Bulletin of the Chemical Society of Japan, 1963, pp. 1408-1411; vol. 36.
Westervelt, "A Study of the Calcium Complex of the Potassium Salt of Catechol-4-Sulfonate in Aqueous, Alkalino Media," Jan. 1981, Doctoral Dissertation, retrieved from https://smartech.gatech.edu/bitstream/handle/1853/5723/westervelt-iii_hh.pdf.
Ahn et al., "A Study of Benzene 1,2,4-Trisphosphate Derivatives as Inositol 1,4,5-Trisphosphate 3-Kinase Inhibitors," Bull. Korean Chem. Soc., 2002, pp. 515-517, vol. 23., No. 3.
Bosch et al., "Novel Catalysis of Hydroquinone Autoxidation with Nitrogen Oxides," J. Org. Chem., 1994, pp. 2529-2536, 59.
Lang et al., "Studies on the Biosynthesis of Bovilactone-4,4 and Related Fungal Meroterpenoids," Eur. J. Org. Chem., 2008, pp. 3544-3551.
Lang et al., "Studies on the Structure and Biosynthesis of Tridentoquinone and Related Meroterpenoids from the Mushroom *Suillus tridentinus* (Boletales)," Eur. J. Org. Chem., 2008, pp. 816-825.
Mcomie et al. "The Thiele-Winter Acetoxylation of Quinones," Organic Reactions, 1972, pp. 199-277, 19, John Wiley and Sons, Inc., New York.
Spyroudis, "Hydroxyquinones: Synthesis and Reactivity," Molecules, 2000, pp. 1291-1330, 5.
W. Maison, et al., "Effect of Calcination Temperature on Phase Transformation and Particle size of Barium Titanate Fine Powders Synthesized by the Catecholate Process," ScienceAsia, 2001, pp. 239-243, 27.
B.A. Borgias, et al., "Synthetic, Structural, and Physical Studies of Titanium Complexes of Catechol and 3,5-Di-tert-butylcatechol," Inorg. Chem., 1984, pp. 1009-1016, 23.
Ali, Synthesis and Properties of Barium Titanate Powder Derived from a Catechol Complex; Br. Ceram. Trans. J.,1987, vol. 86, No. 4, 1987, 113-117.
Wang et al., "Issues in Freeze Drying of Aqueous Solutions," Chinese Journal of Chemical Engineering, 2012, 20(3), pp. 551-559.

PROCESSES FOR FORMING TITANIUM CATECHOL COMPLEXES

CROSS-REFERENCE TO RELATED APPLICATIONS

Not applicable.

STATEMENT REGARDING FEDERALLY SPONSORED RESEARCH OR DEVELOPMENT

Not applicable.

FIELD

The present disclosure generally relates to energy storage and, more specifically, to methods for preparing titanium catechol complexes as active materials for use in energy storage systems.

BACKGROUND

Electrochemical energy storage systems, such as batteries, supercapacitors and the like, have been widely proposed for large-scale energy storage applications. Various battery designs, including flow batteries, have been considered for this purpose. Compared to other types of electrochemical energy storage systems, flow batteries can be advantageous, particularly for large-scale applications, due to their ability to decouple the parameters of power density and energy density from one another.

Flow batteries generally include negative and positive active materials in corresponding electrolyte solutions, which are flowed separately across opposing sides of a membrane or separator in an electrochemical cell containing negative and positive electrodes. The flow battery is charged or discharged through electrochemical reactions of the active materials that occur inside the two half-cells. As used herein, the terms "active material," "electroactive material," "redox-active material" or variants thereof synonymously refer to materials that undergo a change in oxidation state during operation of a flow battery or like electrochemical energy storage system (i.e., during charging or discharging). Although flow batteries hold significant promise for large-scale energy storage applications, they have often been plagued by sub-optimal energy storage performance (e.g., round trip energy efficiency) and limited cycle life, among other factors. Despite significant investigational efforts, no commercially viable flow battery technologies have yet been developed.

Metal-based active materials can often be desirable for use in flow batteries and other electrochemical energy storage systems. Although non-ligated metal ions (e.g., dissolved salts of a redox-active metal) can be used as an active material, it can often be more desirable to utilize coordination complexes for this purpose. As used herein, the terms "coordination complex, "coordination compound," "metal-ligand complex," or simply "complex" synonymously refer to a compound having at least one covalent bond formed between a metal center and a donor ligand. The metal center can cycle between an oxidized form and a reduced form in an electrolyte solution, where the oxidized and reduced forms of the metal center represent states of full charge or full discharge depending upon the particular half-cell in which the coordination complex is present.

Titanium complexes can be particularly desirable active materials for use in flow batteries and other electrochemical energy storage systems, since such metal complexes can provide good half-cell potentials (e.g., less than −0.3 V) and current efficiencies exceeding 85% at high current density values (e.g., greater than 100 mA/cm$^2$). Various catechol complexes of titanium can be particularly desirable active materials, since they are relatively stable complexes and have a significant degree of solubility in aqueous media. Although various methods are available for synthesizing catechol complexes of titanium (also referred to herein as titanium catecholate complexes or titanium catechol complexes), none are presently viable for producing the significant quantities of these complexes needed to support commercial-scale energy storage applications. In addition, concurrent production of extraneous salts during such processes can be problematic.

In view of the foregoing, improved methods for synthesizing titanium catechol complexes to support their use as active materials in energy storage applications would be highly desirable in the art. The present disclosure satisfies the foregoing needs and provides related advantages as well.

SUMMARY

In some embodiments, methods for synthesizing coordination complexes containing titanium are described herein. The methods can include: forming a catechol solution containing a catechol compound and an organic solvent; heating the catechol solution; adding titanium tetrachloride to the catechol solution to form a reaction mixture; reacting the titanium tetrachloride with the catechol compound to evolve HCl gas from the reaction mixture and to form an intermediate titanium catechol complex; and adding an alkaline aqueous solution to the intermediate titanium catechol complex, the alkaline aqueous solution containing an alkali metal base. The alkali metal base converts the intermediate titanium catechol complex into an alkali metal salt form titanium catechol complex that is at least partially dissolved in the aqueous phase.

In other various embodiments, methods for synthesizing coordination complexes containing titanium can include: providing a catechol solution containing a catechol compound and an organic solvent that is water-immiscible; while heating the catechol solution, adding titanium tetrachloride thereto to evolve HCl gas and to form a reaction mixture containing an intermediate titanium catechol complex that is insoluble in the reaction mixture; without isolating the intermediate titanium catechol complex from the reaction mixture, adding an alkaline aqueous solution containing an alkali metal base to the intermediate titanium catechol complex; reacting the alkali metal base with the intermediate titanium catechol complex to form an alkali metal salt form titanium catechol complex that is at least partially dissolved in an aqueous phase; and separating the aqueous phase and an organic phase from one another.

In some embodiments, the present disclosure describes compositions containing titanium catechol complexes that are substantially free of alkali metal halide salts. More specifically, in some embodiments, the present disclosure describes compositions containing an aqueous phase, and an alkali metal salt form titanium catechol complex dissolved in the aqueous phase, in which the composition contains about 0.01 molar equivalents or less of alkali metal halide salts relative to the alkali metal salt form titanium catechol complex.

In still other embodiments, flow batteries having an electrolyte solution containing an alkali metal salt form titanium catechol complex as an active material in an aqueous phase are described herein.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
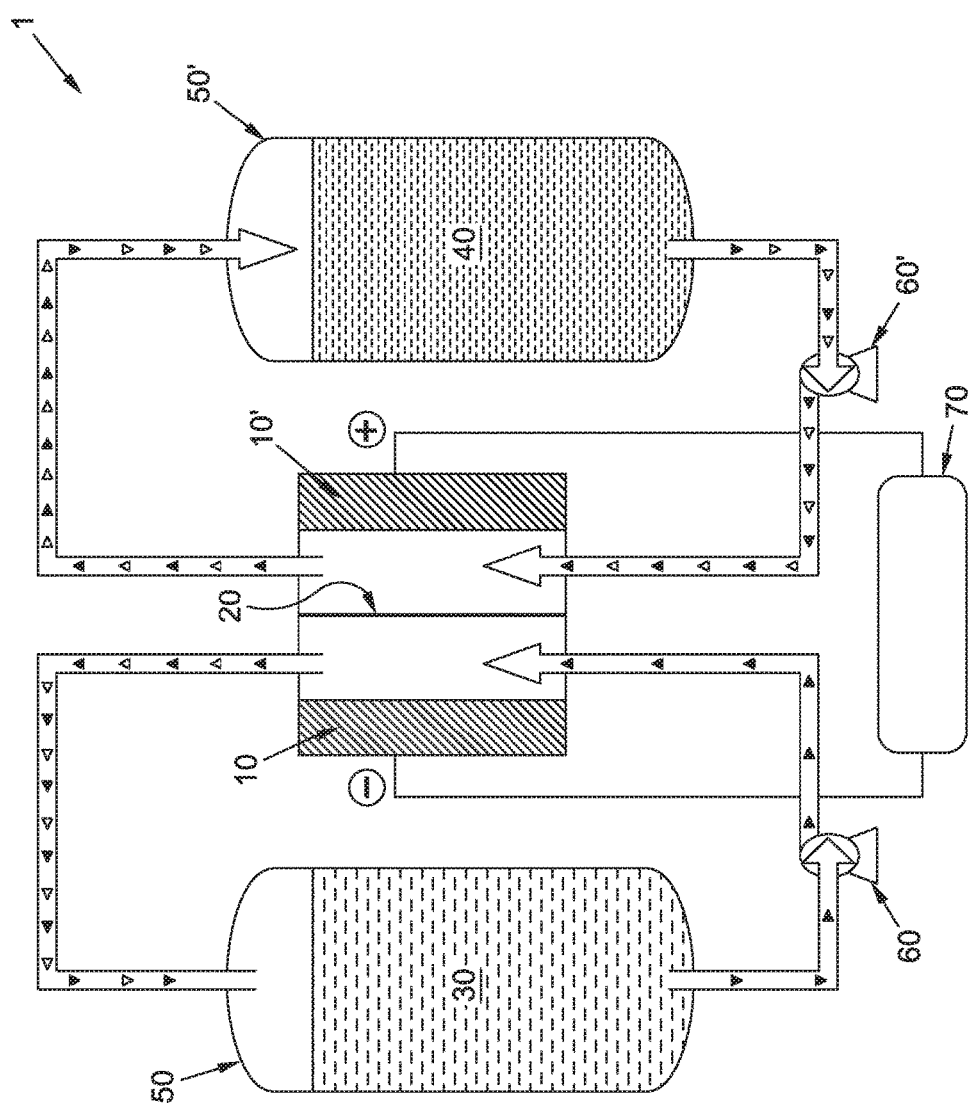
FIG. 1 shows a schematic of an illustrative flow battery.

The present disclosure is directed, in part, to flow batteries and compositions containing alkali metal salt form titanium catechol complexes. The present disclosure is also directed, in part, to methods for synthesizing alkali metal salt form titanium catechol complexes.

The present disclosure may be understood more readily by reference to the following description taken in connection with the accompanying figures and examples, all of which form a part of this disclosure. It is to be understood that this disclosure is not limited to the specific products, methods, conditions or parameters described and/or shown herein. Further, the terminology used herein is for purposes of describing particular embodiments by way of example only and is not intended to be limiting unless otherwise specified. Similarly, unless specifically stated otherwise, any description herein directed to a composition is intended to refer to both solid and liquid versions of the composition, including solutions and electrolytes containing the composition, and electrochemical cells, flow batteries, and other energy storage systems containing such solutions and electrolytes. Further, it is to be recognized that where the disclosure herein describes an electrochemical cell, flow battery, or other energy storage system, it is to be appreciated that methods for operating the electrochemical cell, flow battery, or other energy storage system are also implicitly described.

It is also to be appreciated that certain features of the present disclosure may be described herein in the context of separate embodiments for clarity purposes, but may also be provided in combination with one another in a single embodiment. That is, unless obviously incompatible or specifically excluded, each individual embodiment is deemed to be combinable with any other embodiment(s) and the combination is considered to represent another distinct embodiment. Conversely, various features of the present disclosure that are described in the context of a single embodiment for brevity's sake may also be provided separately or in any sub-combination. Finally, while a particular embodiment may be described as part of a series of steps or part of a more general structure, each step or sub-structure may also be considered an independent embodiment in itself.

Unless stated otherwise, it is to be understood that each individual element in a list and every combination of individual elements in that list is to be interpreted as a distinct embodiment. For example, a list of embodiments presented as "A, B, or C" is to be interpreted as including the embodiments "A," "B," "C," "A or B," "A or C," "B or C," or "A, B, or C."

In the present disclosure, the singular forms of the articles "a," "an," and "the" also include the corresponding plural references, and reference to a particular numerical value includes at least that particular value, unless the context clearly indicates otherwise. Thus, for example, reference to "a material" is a reference to at least one of such materials and equivalents thereof.

In general, use of the term "about" indicates approximations that can vary depending on the desired properties sought to be obtained by the disclosed subject matter and is to be interpreted in a context-dependent manner based on functionality. Accordingly, one having ordinary skill in the art will be able to interpret a degree of variance on a case-by-case basis. In some instances, the number of significant figures used when expressing a particular value may be a representative technique of determining the variance permitted by the term "about." In other cases, the gradations in a series of values may be used to determine the range of variance permitted by the term "about." Further, all ranges in the present disclosure are inclusive and combinable, and references to values stated in ranges include every value within that range.

As discussed above, energy storage systems that are operable on a large scale while maintaining high efficiency values can be extremely desirable. Flow batteries employing coordination complexes as active materials have generated significant interest in this regard. Exemplary description of illustrative flow batteries, their use, and operating characteristics is provided hereinbelow. Titanium coordination complexes, particularly those containing at least one catecholate ligand, can be especially desirable due to their favorable half-cell potentials and high current efficiency values, among other factors. Although various techniques are presently available in the art for synthesizing titanium catechol complexes, none are believed to be suitable for producing high-purity active materials at the very large (multi-pound up to multi-ton) scales needed to support commercial energy storage applications. Raw material costs, labor expenses, low yields and insufficient purity are among the factors that can be problematic at present for supplying commercially viable quantities of these types of active materials.

As indicated above, titanium coordination complexes containing at least one catecholate ligand can be particularly desirable active materials for use in flow batteries and other electrochemical energy storage systems. As used herein, the term "catechol" refers to a compound having an aromatic ring bearing hydroxyl groups on adjacent carbon atoms (i.e., 1,2-hydroxyl groups). Optional substitution can also be present in addition to the 1,2-hydroxyl groups. As used herein, the term "catecholate" refers to a substituted or unsubstituted catechol compound that is bound to a metal center via a metal-ligand bond, particularly a titanium metal center. As used herein, the term "unsubstituted catecholate" refers to the particular case where 1,2-dihydroxybenzene (catechol) is bound to a metal center via a metal-ligand bond. The optional substitution on catecholate ligands can serve a number of purposes such as, for example, altering the solubility characteristics and/or half-cell potentials of the metal complexes that they produce. Monosulfonated catecholate ligands, for example, can improve the solubility of titanium coordination complexes while maintaining desirable electrochemical properties that are at least comparable to those obtained when only unsubstituted catecholate ligands are present. As used herein, the term "monosulfonated" refers to one sulfonic acid group or any salt thereof being present on an aromatic ring. Catecholate ligands bearing an additional hydroxyl group, such as pyrogallol and gallic acid, can be similarly advantageous in this regard.

The present inventor discovered processes for synthesizing titanium catechol complexes that can proceed from readily available and relatively inexpensive starting materials. Namely, the syntheses described herein employ titanium tetrachloride as a readily available titanium source and take place using common organic solvents. Such syntheses can be conducted on a wide range of scales, ranging from gram-scale laboratory processes up to multi-ton production. Advantageously, these processes allow the titanium catechol complexes to be obtained at high purity levels in high-concentration aqueous solutions that can be suitable for use in flow batteries and other electrochemical energy storage systems with little to no further processing. In particular, the processes described herein allow the titanium catechol complexes to be produced without forming significant amounts of alkali metal halide salts, particularly sodium chloride.

More specifically, the syntheses described herein allow an intermediate titanium catechol complex to be initially formed through reacting titanium tetrachloride with a catechol compound in an organic solvent. In many organic solvents, the intermediate titanium catechol complex precipitates from the reaction mixture, which helps drive the reaction toward complete conversion of the starting materials. Since the reaction stops at an insoluble intermediate stage, HCl gas, formed as a co-product of the reaction, can be driven off to substantial completion, which can be especially advantageous for converting the intermediate titanium catechol complex into a final product form, such as a solution of the titanium catechol complex, as discussed further herein. Further advantageously, the intermediate titanium catechol complex need not be isolated before converting to the final product form, although it can be, if desired.

In particular, the intermediate titanium catechol complex can be converted into an alkali metal salt form titanium catechol complex through reaction with an alkaline aqueous solution containing an alkali metal base. As used herein, the term "alkali metal" refers to a metal in Group I of the periodic table, such as sodium or potassium. Although an alkali metal salt form titanium catechol complex can be advantageous for use in conjunction with the components of flow batteries and other electrochemical systems, it is to be recognized that alternative salt forms, such as alkaline earth metal salt form titanium catechol complexes, can be synthesized by using an alkaline earth metal base, such as calcium hydroxide. Other metal salt forms can also be prepared similarly. In more particular embodiments, the alkali metal base can be an alkali metal hydroxide. Unlike the intermediate titanium catechol complex, the alkali metal salt form titanium catechol complex is readily soluble in the aqueous phase resulting from addition of the alkaline aqueous solution to the intermediate titanium catechol complex. By carefully controlling the stoichiometric quantity of alkali metal base that is added to the intermediate titanium catechol complex (based on the molar amount of titanium tetrachloride that is initially present), a desired pH can be obtained in the aqueous phase resulting from conversion of the intermediate titanium catechol complex. Moreover, because the syntheses described herein allow substantial removal of all HCl gas to take place from the reaction mixture before adding the alkaline aqueous solution thereto, essentially all of the alkali metal base can go toward converting the intermediate titanium catechol complex into the corresponding alkali metal salt form rather than forming an alkali metal halide salt, specifically sodium chloride or potassium chloride, in the aqueous phase. Avoiding the formation of alkali metal halide salts in the aqueous phase can be desirable in order to maintain high solubility levels for the alkali metal salt form titanium catechol complex, which might otherwise be decreased due to a common ion effect in the presence of extraneous alkali metal halide salts. In some embodiments, alkali metal halide salts can be present at levels of about 0.01 equivalents or less relative to the alkali metal salt form titanium catechol complex in the aqueous phases produced by the methods described herein.

As a further advantage, by utilizing an organic solvent that is immiscible with water, the resulting aqueous phase containing the alkali metal salt form titanium catechol complex can be readily isolated by various phase partitioning techniques. Because minimal workup is needed when an immiscible solvent is used, production runs can provide large quantities of product in a relatively short amount of time. Accordingly, the syntheses described herein are readily amenable to scale up to a desired level. Further, the syntheses described herein can be readily extended to continuous syntheses, rather than batchwise processes. Although organic solvents that are immiscible with water can be advantageous for the reasons noted above, water-miscible organic solvents can also be suitable and advantageous in some instances, as described further herein.

In various embodiments, the present disclosure describes methods including: forming a catechol solution containing a catechol compound and an organic solvent; heating the catechol solution; adding titanium tetrachloride to the catechol solution to form a reaction mixture; reacting the titanium tetrachloride with the catechol compound to evolve HCl gas from the reaction mixture and to form an intermediate titanium catechol complex; and adding an alkaline aqueous solution to the intermediate titanium catechol complex, the alkaline aqueous solution including an alkali metal base. The alkali metal base converts the intermediate titanium catechol complex into an alkali metal salt form titanium catechol complex that is at least partially dissolved in an aqueous phase.

In further embodiments, the methods can include separating the aqueous phase and an organic phase from one another. The aqueous phase can be substantially free of alkali metal halide salts, such as sodium chloride or potassium chloride, as discussed herein. Suitable techniques for separating the aqueous phase can include various solvent partitioning techniques, which can be predicated upon the use of an organic solvent that is substantially water-immiscible.

Catechol compounds suitable for use in the various embodiments described herein are not considered to be particularly limited. In some embodiments, the catechol compound can be o-catechol itself (i.e., unsubstituted 1,2-dihydroxybenzene). In some or other embodiments, the catechol compound can include at least one substituted catechol compound, which can optionally be present in combination with an unsubstituted catechol compound. Accordingly, the alkali metal salt form titanium catechol complexes described herein can include unsubstituted catecholate ligands, substituted catecholate ligands, or any combination thereof. In particular embodiments, 3,4-dihydroxybenzenesulfonic acid can be an especially desirable substituted catechol compound for use in forming an alkali metal salt form titanium catechol complex. Pyrogallol and gallic acid are also substituted catechol compounds that can be particularly desirable.

Other examples of substituted catechol compounds that can be suitable for use in the embodiments described herein can include those bearing solubilizing groups to increase the aqueous solubility of the resulting complexes. Non-limiting examples of substituted catechol compounds that can be suitable for use in the embodiments described herein can include those having a structure of

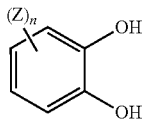

in a neutral form or a salt form. Z is a heteroatom functional group selected from the group consisting of $A^1R^{41}$, $A^2R^{42}$, $A^3R^{43}$, CHO, and sulfonic acid. Variable n is an integer ranging between 1 and 4, such that one or more Z are bound to the substituted catechol compound at an open aromatic ring position. Each Z is the same or different when more than one Z is present. $A^1$ is —$(CH_2)_a$— or —$(CHOR)(CH_2)_a$—, $R^{41}$ is —$OR^1$ or —$(OCH_2CH_2O)_bR^1$, a is an integer ranging between 0 and about 6, and b is an integer ranging between 1 and about 10. $A^2$ is —$(CH_2)_c$— or —$CH(OR^2)(CH_2)_d$—, $R^{42}$ is —$NR^3R^4$, a carbon-linked amino acid, or —$C(=O)$ $XR^5$, X is —O— or —$NR^6$—, c is an integer ranging between 0 and about 6, and d is an integer ranging between 0 and about 4. $A^3$ is —O— or —$NR^2$—, $R^{43}$ is —$(CHR^7)_eOR^1$, —$(CHR^7)_eNR^3R^4$, —$(CHR^7)_eC(=O)XR^5$, or —$C(=O)(CHR^7)_fR^8$, e is an integer ranging between 1 and about 6, and f is an integer ranging between 0 and about 6. R is H, $C_1$-$C_6$ alkyl, heteroatom-substituted $C_1$-$C_6$ alkyl, or $C_1$-$C_6$ carboxyalkyl. $R^1$ is H, methyl, ethyl, a $C_2$-$C_6$ polyol bound through an ether linkage or an ester linkage, or $C_1$-$C_6$ carboxyalkyl. $R^2$, $R^3$, $R^4$ and $R^6$ are independently selected from the group consisting of H, $C_1$-$C_6$ alkyl, or heteroatom-substituted $C_1$-$C_6$ alkyl. $R^5$ is H, $C_1$-$C_6$ alkyl, heteroatom-substituted $C_1$-$C_6$ alkyl, a $C_2$-$C_6$ polyol bound through an ester linkage, a hydroxyacid bound through an ester linkage, a polyglycol acid bound through an ester linkage, an amino alcohol bound through an ester linkage or an amide linkage, an amino acid bound through an ester linkage or an amide linkage, or —$(CH_2CH_2O)_bR^1$. $R^7$ is H or OH. $R^8$ is H, $C_1$-$C_6$ alkyl, heteroatom-substituted $C_1$-$C_6$ alkyl, a $C_2$-$C_6$ polyol bound through an ether linkage or an ester linkage, a hydroxyacid bound through an ether linkage or an ester linkage, a polyglycol acid bound through an ether linkage or an ester linkage, an amino alcohol bound through an ether linkage, an ester linkage, or an amide linkage, an amino acid bound through an ether linkage, an ester linkage, or an amide linkage, a carbon-linked amino acid, or —$(OCH_2CH_2O)_bR^1$.

Without being bound by any theory or mechanism, it is believed that the intermediate titanium catechol complex produced in the embodiments of the present disclosure has a formula of $$H_2Ti(L)_3,$$

wherein L represents a catecholate ligand, an unsubstituted catecholate ligand or any combination thereof. That is, the intermediate titanium catechol complex is believed to be a "protonated" counterion pair of a titanium-based complex anion. As discussed below, in some embodiments, other ligands can also be present in combination with substituted or unsubstituted catecholate ligands. That is, the entire quantity of L need not necessarily be a catecholate ligand in the embodiments described herein.

As indicated above, the intermediate titanium catechol complex can be converted into an alkali metal salt form titanium catechol complex through reaction with an alkali metal base. Again remaining unbound by any theory or mechanism, it is believed that such alkali metal salt form titanium catechol complexes can have a formula of $$D_2Ti(L)_3,$$

wherein D is an alkali metal ion or any combination thereof, and L is defined as above. When the alkaline aqueous solution contains a base that is not an alkali metal base, such as an alkaline earth metal base, D can also include any alternative metal ions (e.g, a single alkaline earth metal ion or a mixture of alkaline earth metal ions), optionally in combination with one or more alkali metal ions. In some embodiments, a single type of substituted or unsubstituted catechol compound can be present in the complexes. In other embodiments, mixtures of two or more unsubstituted and/or substituted catechol compounds can be present. In still other embodiments, ligands that are non-catecholate ligands can be present. For example, in some embodiments, the alkali metal salt form titanium catechol complexes can have a formula of $$D_2Ti(L_1)(L_2)(L_3),$$

wherein D is an alkali metal ion or any combination thereof, optionally in combination with other metal ions, and $L_1$-$L_3$ are ligands, provided that at least one of $L_1$-$L_3$ is a catecholate ligand or a substituted catecholate ligand. Alternative ligands that can constitute the balance of $L_1$-$L_3$ include, but are not limited to, certain exemplary ligands described hereinbelow.

In more specific embodiments, alkali metal salt form titanium catechol complexes of the present disclosure can have a formula of $$Na_mK_nTi(L)_3,$$

wherein m+n=2, provided that L does not bear a charged functional group, and L is defined as above. For example, in the case of at least one catecholate ligand (L) bearing a negatively charged functional group, such as a sulfonic acid anion, greater than two molar equivalents of sodium and/or potassium ions are needed to maintain charge balance. In more particular embodiments, both m and n are non-zero numbers, and they can be equal or non-equal to one another. In some embodiments, a ratio of m to n can range between about 1:10 to about 10:1, or between about 1:5 or about 5:1. In some embodiments, substantially equal molar quantities of sodium and potassium can be present in the alkali metal salt form titanium catechol complexes. As indicated above, non-catecholate ligands can also be present in such complexes.

Accordingly, in some embodiments of the present disclosure, the alkali metal base can include an alkali metal hydroxide such as sodium hydroxide, potassium hydroxide, or any combination thereof. In more particular embodiments, the alkali metal base can be a mixture of sodium hydroxide and potassium hydroxide. The molar ratios of the sodium hydroxide and potassium hydroxide can lie within the ranges disclosed above. Complexes having mixed sodium and potassium counterions can be especially desirable due to their potentially increased solubility values compared to those obtained when a single alkali metal counterion is present.

In alternative embodiments of the present disclosure, alkali metal bases such as alkali metal oxides, alkali metal carbonates, and alkali metal bicarbonates can be used to convert the intermediate titanium catechol complex into the alkali metal salt form titanium catechol complex. Optionally, these alkali metal bases can be used in combination with the alkali metal hydroxide bases discussed above. Again, a mixture of sodium and potassium counterions can be introduced through the choice of the alkali metal bases present in the alkaline aqueous solution. For example, an alkali metal hydroxide having a first alkali metal counterion can be combined with an alkali metal carbonate or bicarbonate having a second alkali metal counterion to accomplish the foregoing.

As still another alternative to alkali metal hydroxide bases, ammonium bases, such as ammonium hydroxide, can also be used in some embodiments of the present disclosure. In some embodiments, the alkaline aqueous solution can contain a mixture of ammonium hydroxide and an alkali metal base, in which case the resulting titanium catechol complex can contain a mixture of ammonium and alkali metal counterions.

In some embodiments, ligands in addition to substituted or unsubstituted catecholate ligands can be present in the complexes described herein. Other ligands that can be present in combination with catecholate ligands include, for example, ascorbate, citrate, glycolate, a polyol, gluconate, hydroxyalkanoate, acetate, formate, benzoate, malate, maleate, phthalate, sarcosinate, salicylate, oxalate, urea, polyamine, aminophenolate, acetylacetonate, and lactate. Where chemically feasible, it is to be recognized that such ligands can be optionally substituted with at least one group selected from among $C_{1-6}$ alkoxy, $C_{1-6}$ alkyl, $C_{1-6}$ alkenyl, $C_{1-6}$ alkynyl, 5- or 6-membered aryl or heteroaryl groups, a boronic acid or a derivative thereof, a carboxylic acid or a derivative thereof, cyano, halide, hydroxyl, nitro, sulfonate, a sulfonic acid or a derivative thereof, a phosphonate, a phosphonic acid or a derivative thereof, or a glycol, such as polyethylene glycol. Alkanoate includes any of the alpha, beta, and gamma forms of these ligands. Polyamines include, but are not limited to, ethylenediamine, ethylenediamine tetraacetic acid (EDTA), and diethylenetriamine pentaacetic acid (DTPA).

Other examples of ligands that can be present in the complexes of the present disclosure can include monodentate, bidentate, and/or tridentate ligands. Examples of monodentate ligands that can be present in the complexes of the present disclosure include, for example, carbonyl or carbon monoxide, nitride, oxo, hydroxo, water, sulfide, thiols, pyridine, pyrazine, and the like. Examples of bidentate ligands that can be present in the complexes of the present disclosure include, for example, bipyridine, bipyrazine, ethylenediamine, diols (including ethylene glycol), and the like. Examples of tridentate ligands that can be present in the complexes of the present disclosure include, for example, terpyridine, diethylenetriamine, triazacyclononane, tris(hydroxymethyl)aninomethane, and the like.

In some embodiments, the titanium tetrachloride can be added neat to the catechol solution in the organic solvent. In other embodiments, a solution of titanium tetrachloride in an organic solvent can be added to the catechol solution. Depending upon the scale at which the reaction is run, adding a solution of titanium tetrachloride can facilitate transfer of this reagent compared to neat transfer. For example, at smaller reaction scales, where the amount of titanium tetrachloride is smaller, transferring a solution of titanium tetrachloride can be easier to accomplish.

Suitable organic solvents for utilization in the various embodiments described herein are not considered to be particularly limited. In some embodiments, the organic solvent can be non-reactive toward titanium tetrachloride and substantially water-immiscible. Non-limiting examples of suitable organic solvents include aprotic organic solvents that are water-immiscible such as toluene, xylenes, benzene, ligroin, hexane, cyclohexane, dichloromethane, dichloromethane, ethyl ether, isopropyl ether, methyl t-butyl ether, and any combination thereof. Water-immiscible organic solvents of this type can be particularly desirable for their utility in processing the intermediate titanium catechol complex into the alkali metal salt form titanium catechol complex, as discussed further hereinafter. In addition, such water-immiscible organic solvents do not have significant affinity for retaining HCl gas formed during the reaction between the catechol compound and titanium tetrachloride, thereby allowing this reaction co-product to be substantially driven off from the reaction mixture prior to adding the alkaline aqueous solution to transform the intermediate titanium catechol complex into the alkali metal salt form titanium catechol complex.

In some embodiments, organic solvents that have some measure of water miscibility can also be suitable. In this regard, suitable organic solvents can include, for example, tetrahydrofuran (THF), acetonitrile, dioxane, dimethylformamide, dimethylsulfoxide, and any combination thereof. Water-miscible organic solvents can be used alone in some embodiments, or they can be used in combination with a water-immiscible organic solvent in other embodiments. In the case where a water-miscible organic solvent is used, the aqueous phase resulting from formation of the alkali metal salt form titanium catechol complex can retain at least a portion of the organic solvent therein. Residual organic solvent in the aqueous phase can improve solubility of the alkali metal salt form titanium catechol complex in some instances. If the presence of organic solvent in the aqueous phase is undesired, however, the residual solvent can be removed from the aqueous phase by various distillation processes. Distillation can also be used to remove trace quantities of admixed water-immiscible organic solvents, if needed or desired.

In still other embodiments, alcohol solvents can be suitable for use in the syntheses described herein. Although alcohol solvents are reactive with titanium tetrachloride to produce titanium alkoxides, the titanium alkoxides can further react to form a titanium catechol complex in accordance with the present disclosure. In some embodiments, alcohol solvents can be used in combination with any of the other organic solvents mentioned above.

As indicated above, suitable organic solvents for conducting the syntheses described herein can lack significant affinity for retaining HCl gas, thereby allowing the HCl gas to be substantially removed from the reaction mixture before adding the alkaline aqueous solution to the intermediate titanium catechol complex. Removal of the HCl gas allows the alkali metal salt form titanium catechol complex to be formed in an aqueous phase without generating an appreciable amount of alkali metal chloride salts, which can be desirable for improving solubility of the complex. Additional measures can also be taken to ensure that residual quantities of HCl gas are removed from the reaction mixture before adding the alkaline aqueous solution thereto and forming the alkali metal salt form titanium catechol complex. Reduced pressure, inert gas purge, heat or any combination thereof may be employed to remove residual HCl gas, as discussed hereinafter.

In some embodiments, the reaction mixture can be maintained at a reduced pressure before adding the alkaline aqueous solution thereto. As used herein, the term "reduced pressure" refers to any pressure below normal atmospheric pressure, which is 760 torr at sea level. In some embodiments, suitable reduced pressures for removing HCl gas from the reaction mixture can range between about 50 torr and about 400 torr, or between about 100 torr and about 200 torr. The normal boiling point of the organic solvent can dictate to some extent how much the pressure can be reduced to affect removal of HCl gas from the reaction mixture. In general, the pressure should be maintained such that loss of the organic solvent is minimal. For example, in the case of lower boiling solvents such as dichloromethane, higher pressures may be needed to preclude solvent loss compared to those that can be utilized when employing higher boiling solvents, such as xylenes.

In some embodiments, a flowing inert gas can contact the reaction mixture while evolving the HCl gas therefrom. Suitable inert gases can include, for example, nitrogen, helium, argon, neon, or the like. Similar to the reduced pressure operations discussed above, the flowing inert gas can promote removal of HCl gas from the reaction mixture.

In most instances, the intermediate titanium catechol complex is insoluble in the reaction mixture in the syntheses described herein. As indicated above, precipitation of the intermediate titanium catechol complex can help drive the reaction to completion, as well as provide a visual indicator of when the reaction is complete. For most aprotic organic solvents that are substantially water-immiscible, the intermediate titanium catechol complex is insoluble, which can make these organic solvents especially desirable for use in the embodiments of the present disclosure. The intermediate titanium catechol complex is also insoluble in some water-miscible solvents, and such solvents can also be desirable for use in some embodiments described herein, such as instances wherein some residual organic solvent in the aqueous phase can be tolerated.

In principle, the intermediate titanium catechol complex can be isolated from the reaction mixture and undergo optional purification before being combined with the alkaline aqueous solution. Isolation and/or purification can be particularly facile in instances where the intermediate titanium catechol complex is insoluble in the organic solvent. Isolation and/or purification of the intermediate titanium catechol complex can provide another measure for removal of residual HCl gas that would otherwise form alkali metal chloride salts upon converting the intermediate titanium catechol complex into the alkali metal salt form titanium catechol complex. Isolation and purification of the intermediate titanium catechol complex can also be performed if residual quantities of the organic solvent are undesirable when forming the aqueous phase containing the alkali metal salt form titanium catechol complex or if removal of residual quantities of organic solvent would be problematic or expensive. Additional impurities, such as reaction byproducts and unreacted starting materials, can also be removed though isolation of the intermediate titanium catechol complex before its conversion into the alkali metal salt form.

More desirably, however, the intermediate titanium catechol complex can be reacted in situ without isolation from the reaction mixture before adding the alkaline aqueous solution thereto. In situ reaction of the intermediate titanium catechol complex can be less labor intensive and less costly compared to instances where additional isolation and purification operations are performed. In more specific embodiments, the intermediate titanium catechol complex and the alkali metal salt form titanium catechol complex can be formed consecutively in a single reaction vessel.

An amount of the alkali metal base in the alkaline aqueous solution can be chosen such that it is sufficient to convert the intermediate titanium catechol complex into its corresponding alkali metal salt form in an aqueous phase. The amount of alkali metal base can be chosen to be stoichiometrically equivalent to that of the titanium tetrachloride initially present, or the alkali metal base can be present in a slight stoichiometric excess or deficit. Accordingly, the resulting aqueous phase containing the alkali metal salt form titanium catechol complex can be neutral, modestly basic or modestly acidic, depending upon the actual amount of alkali metal base present and the yield at which the intermediate titanium catechol complex formed. Since the synthetic methods described herein allow HCl gas to be substantially removed from the reaction mixture, essentially none of the alkali metal base is consumed to form unwanted alkali metal chlorides. Further, since a high percentage of the titanium tetrachloride undergoes conversion into the intermediate titanium catechol complex, the a good estimate of the aqueous phase pH can be obtained based upon the initial molar amount of titanium tetrachloride that is present and the molar amount of added alkali metal base.

In more particular embodiments, an amount of the alkali metal base in the alkaline aqueous solution is such that the aqueous phase containing the alkali metal salt form titanium catechol complex has a pH of about 6 to about 8. In still more particular embodiments, an amount of the alkali metal base can be chosen such that the resulting aqueous phase has a pH of about 7 to about 8. Attaining an initial pH that is not far removed from neutral allows the alkali metal salt form titanium catechol complex to be formed and maintained in the aqueous phase under pH conditions where it is relatively stable. In addition, an initial pH within this range can be readily adjusted upwardly without introducing alkali metal halides to the aqueous phase, as described hereinafter. That is, by forming an aqueous phase having a near-neutral pH at which the alkali metal salt form titanium catechol complex is stable, more careful pH adjustment can than take place afterward. In contrast, if excess alkaline aqueous solution was added to convert the intermediate titanium catechol complex into the corresponding alkali metal salt form, the initial pH would be higher. Although the alkali metal salt form titanium catechol complex might well be stable at this higher pH, the pH could not be lowered with an acid without introducing extraneous sodium and/or potassium salts in the aqueous solution. For example, lowering the initial pH with hydrochloric acid would result in the unwanted production of sodium chloride or potassium chloride within the aqueous phase, which can be desirable to avoid for the reasons noted above. Accordingly, in some embodiments, the initial pH can be adjusted by adding an additional quantity of the alkaline aqueous solution or a different alkaline aqueous solution to adjust the pH to a range of about 9 to about 10, or about 10 to about 12, or about 12 to about 14. The pH range can be chosen depending upon the particular application in which the aqueous phase is to be employed.

Accordingly, in some or other more specific embodiments, methods for synthesizing compositions containing an alkali metal salt form titanium catechol complex can include: providing a catechol solution containing a catechol compound and an organic solvent that is water-immiscible; while heating the catechol solution, adding titanium tetrachloride thereto to evolve HCl gas and to form a reaction mixture containing an intermediate titanium catechol complex that is insoluble in the reaction mixture; without isolating the intermediate titanium catechol complex from the reaction mixture, adding an alkaline aqueous solution containing an alkali metal base to the intermediate titanium catechol complex; reacting the alkali metal base with the intermediate titanium catechol complex to form an alkali metal salt form titanium catechol complex that is at least partially dissolved in an aqueous phase; and separating the aqueous phase and an organic phase from one another. In more particular embodiments, heating is continued after adding the alkaline aqueous solution to the reaction mixture.

In various embodiments of the present disclosure, the aqueous phase containing the alkali metal salt form titanium catechol complex can have a concentration of the complex of about 0.5 M or above. In more particular embodiments, the concentration of the alkali metal salt form titanium catechol complex can range between about 0.5 M and about 2 M, or a between about 0.75 M and about 1.5 M or between about 1 M and about 2 M.

Therefore, in some or other various embodiments, the present disclosure provides compositions containing titanium catechol complexes. In more specific embodiments, the compositions described herein can include an aqueous phase, and an alkali metal salt form titanium catechol complex dissolved in the aqueous phase, in which the composition contains about 0.01 molar equivalents or less of alkali metal halide salts relative to the alkali metal salt form titanium catechol complex. In more specific embodiments, the aqueous phase can be substantially free of alkali metal halide salts, particularly sodium chloride. As discussed above, the synthetic processes described hereinabove allow aqueous phases of this type to be readily prepared.

In some embodiments, the aqueous phase can be substantially free of an organic solvent. The organic solvent that is excluded from the aqueous phase can be that which was used in conjunction with forming the intermediate titanium catechol complex. Water-immiscible organic solvents can be readily excluded. Additional distillation can be conducted to remove the organic solvent from the aqueous phase, if needed.

In other embodiments, the aqueous phase formed in accordance with the disclosure above can contain at least some amount of organic solvent. In some embodiments, the aqueous phase can contain trace or non-trace amounts of an organic solvent that was used in conjunction with forming the intermediate titanium catechol complex. In such embodiments, the organic solvent can be a water-miscible aprotic organic solvent that is non-reactive with titanium tetrachloride, such as those discussed above. In some or other embodiments, a quantity of organic solvent can be added to the aqueous phase after its formation. Organic solvents added to the aqueous phase after its formation can include water-miscible organic solvents that are either reactive or non-reactive with titanium tetrachloride. In more particular embodiments, alcohol or glycol solvents can be added to the aqueous phase after its formation.

In more specific embodiments, the aqueous phase can contain at least about 98% water by weight. In other more specific embodiments, the aqueous phase can contain at least about 55% water by weight, or at least about 60% water by weight, or at least about 65% water by weight, or at least about 70% water by weight, or at least about 75% water by weight, or at least about 80% water by weight, or at least about 85% water by weight, or at least about 90% water by weight, or at least about 95% water by weight. In some embodiments, the aqueous phase can be free of water-miscible organic solvents and consist of water alone as a solvent for the alkali metal salt titanium catechol complex In further embodiments, the aqueous phase can include a viscosity modifier, a wetting agent, a buffer, or any combination thereof. Suitable viscosity modifiers can include, for example, corn starch, corn syrup, gelatin, glycerol, guar gum, pectin, and the like. Other suitable examples will be familiar to one having ordinary skill in the art. Suitable wetting agents can include, for example, various non-ionic surfactants and/or detergents. In some or other embodiments, the aqueous phase can further include a glycol or a polyol. Suitable glycols can include, for example, ethylene glycol, diethylene glycol, and polyethylene glycol. Suitable polyols can include, for example, glycerol, mannitol, sorbitol, pentaerythritol, and tris(hydroxymethyl)aminomethane. Illustrative buffers that can be present include, but are not limited to, salts of phosphates, borates, carbonates, silicates, tris(hydroxymethyl)aminomethane (TRIS), 4-(2-hydroxyethyl)-1-piperazineethanesulfonic acid (HEPES), piperazine-N,N'-bis(ethanesulfonic acid) (PIPES), or any combination thereof. Inclusion of any of these components in the aqueous phase can help maintain the alkali metal salt form titanium catechol complex in a dissolved form and/or facilitate the incorporation of the aqueous phase in a flow battery, for example.

In some embodiments, the aqueous phase described herein can further include one or more mobile ions (i.e., an extraneous electrolyte) for use as an electrolyte solution in a flow battery or similar electrochemical system. In some embodiments, suitable mobile ions can include proton, hydronium, or hydroxide. In other various embodiments, mobile ions other than proton, hydronium, or hydroxide can be present, either alone or in combination with proton, hydronium or hydroxide. Such alternative mobile ions can include, for example, alkali metal or alkaline earth metal cations (e.g., $Li^+$, $Na^+$, $K^+$, $Mg^{2+}$, $Ca^{2+}$ and $Sr^{2+}$) and halides (e.g., $F^-$, $Cl^-$, or $Br^-$). Other suitable mobile ions can include, for example, ammonium and tetraalkylammonium ions, chalcogenides, phosphate, hydrogen phosphate, phosphonate, nitrate, sulfate, nitrite, sulfite, perchlorate, tetrafluoroborate, hexafluorophosphate, and any combination thereof. In some embodiments, less than about 50% of the mobile ions can constitute protons, hydronium, or hydroxide. In other various embodiments, less than about 40%, less than about 30%, less than about 20%, less than about 10%, less than about 5% or less than about 2% of the mobile ions can constitute protons, hydronium, or hydroxide. In other various embodiments, aqueous phases containing the alkali metal salt form titanium catechol complexes of the present disclosure can lack an extraneous electrolyte altogether.

As indicated above, the alkali metal salt form titanium catechol complexes of the present disclosure and related aqueous phases containing these complexes can be incorporated in flow batteries and related electrochemical systems. Further disclosure on suitable flow batteries and their operating parameters follows hereinafter.

In various embodiments, flow batteries of the present disclosure can include a first half-cell having a first electrolyte solution therein, in which the first electrolyte solution is an aqueous phase containing an alkali metal salt form titanium catechol complex containing about 0.01 molar equivalents or less of alkali metal halides relative to the alkali metal salt form titanium catechol complex. More specific disclosure regarding the alkali metal salt form titanium catechol complexes is provided above.

In further embodiments, flow batteries of the present disclosure can also include a second half-cell having a second electrolyte solution therein, where the second electrolyte solution contains an active material differing from that in the first electrolyte solution. In more specific embodiments, the second electrolyte solution can be an aqueous solution containing an iron hexacyanide complex. Iron hexacyanide complexes can be particularly desirable active materials due to their facile electrode kinetics and substantially reversible electrochemical behavior within the working electrochemical window of aqueous solutions. Hence, these complexes can allow high open circuit potentials and cell efficiencies to be realized, particularly in combination with an alkali metal salt form titanium catechol complex as the active material in the first electrolyte solution. In more specific embodiments, flow batteries of the present disclosure can include the first electrolyte solution in contact with a negative electrode of the flow battery and the second electrolyte solution in contact with the positive electrode of the flow battery.

Illustrative flow battery configurations will now be described in further detail. The flow batteries of the present disclosure are, in some embodiments, suited to sustained charge or discharge cycles of several hour durations. As such, they can be used to smooth energy supply/demand profiles and provide a mechanism for stabilizing intermittent power generation assets (e.g., from renewable energy sources such as solar and wind energy). It should be appreciated, then, that various embodiments of the present disclosure include energy storage applications where such long charge or discharge durations are desirable. For example, in non-limiting examples, the flow batteries of the present disclosure can be connected to an electrical grid to allow renewables integration, peak load shifting, grid firming, baseload power generation and consumption, energy arbitrage, transmission and distribution asset deferral, weak grid support, frequency regulation, or any combination thereof. When not connected to an electrical grid, the flow batteries of the present disclosure can be used as power sources for remote camps, forward operating bases, off-grid telecommunications, remote sensors, the like, and any combination thereof. Further, while the disclosure herein is generally directed to flow batteries, it is to be appreciated that other electrochemical energy storage media can incorporate the aqueous phases described herein, specifically those utilizing stationary electrolyte solutions.

In some embodiments, flow batteries of the present disclosure can include: a first chamber containing a negative electrode contacting a first aqueous electrolyte solution; a second chamber containing a positive electrode contacting a second aqueous electrolyte solution, and a separator disposed between the first and second electrolyte solutions. The first aqueous electrolyte solution can be an aqueous phase containing an alkali metal salt form titanium catechol complex, as described above. The chambers provide separate reservoirs within the cell, through which the first and/or second electrolyte solutions circulate so as to contact the respective electrodes and the separator. Each chamber and its associated electrode and electrolyte solution define a corresponding half-cell. The separator provides several functions which include, for example, (1) serving as a barrier to mixing of the first and second electrolyte solutions, (2) electrically insulating to reduce or prevent short circuits between the positive and negative electrodes, and (3) to facilitate ion transport between the positive and negative electrolyte chambers, thereby balancing electron transport during charge and discharge cycles. The negative and positive electrodes provide a surface where electrochemical reactions can take place during charge and discharge cycles. During a charge or discharge cycle, electrolyte solutions can be transported from separate storage tanks through the corresponding chambers. In a charging cycle, electrical power can be applied to the cell such that the active material contained in the second electrolyte solution undergoes a one or more electron oxidation and the active material in the first electrolyte solution undergoes a one or more electron reduction. Similarly, in a discharge cycle the second active material is reduced and the first active material is oxidized to generate electrical power.

In more specific embodiments, illustrative flow batteries of the present disclosure can include: (a) a first aqueous electrolyte solution containing a first coordination complex: (b) a second aqueous electrolyte solution containing a second coordination complex; (c) a separator positioned between said first and second aqueous electrolyte solutions; and (d) an optional mobile ion in the first and second aqueous electrolyte solutions. As described in more detail below, the separator can be an ionomer membrane, and it can have a thickness of less than 100 microns and have an associated net charge that is the same sign as that of the first and second coordination complexes.

FIG. 1 depicts a schematic of an illustrative flow battery. Unlike typical battery technologies (e.g., Li-ion. Ni-metal hydride, lead-acid, and the like), where active materials and other components are housed in a single assembly, flow batteries transport (e.g., via pumping) redox-active energy storage materials from storage tanks through an electrochemical stack. This design feature decouples the electrical energy storage system power from the energy storage capacity, thereby allowing for considerable design flexibility and cost optimization.

As shown in FIG. 1, flow battery system 1 includes an electrochemical cell that features separator 20 (e.g., a membrane) that separates the two electrodes 10 and 10' of the electrochemical cell. Electrodes 10 and 10' are formed from a suitably conductive material, such as a metal, carbon, graphite, and the like. Tank 50 contains first active material 30, which is capable of being cycled between an oxidized state and a reduced state.

Pump 60 affects transport of first active material 30 from tank 50 to the electrochemical cell. The flow battery also suitably includes second tank 50' that contains second active material 40. Second active material 40 can be the same material as active material 30, or it can be different. Second pump 60' can affect transport of second active material 40 to the electrochemical cell. Pumps can also be used to affect transport of the active materials from the electrochemical cell back to tanks 50 and 50' (not shown in FIG. 1). Other methods of affecting fluid transport, such as siphons, for example, can also suitably transport first and second active materials 30 and 40 into and out of the electrochemical cell. Also shown in FIG. 1 is power source or load 70, which completes the circuit of the electrochemical cell and allows a user to collect or store electricity during its operation.

It should be understood that FIG. 1 depicts a specific, non-limiting embodiment of a flow battery. Accordingly, flow batteries consistent with the spirit of the present disclosure can differ in various aspects relative to the configuration of FIG. 1. As one example, a flow battery system can include one or more active materials that are solids, gases, and/or gases dissolved in liquids. Active materials can be stored in a tank, in a vessel open to the atmosphere, or simply vented to the atmosphere.

As used herein, the terms "separator" and "membrane" refer to an ionically conductive and electrically insulating material disposed between the positive and negative electrodes of an electrochemical cell. The separator can be a porous membrane in some embodiments and/or an ionomer membrane in other various embodiments. In some embodiments, the separator can be formed from an ionically conductive polymer.

Polymer membranes can be anion- or cation-conducting electrolytes. Where described as an "ionomer," the term refers to polymer membrane containing both electrically neutral repeating units and ionized repeating units, where the ionized repeating units are pendant and covalently bonded to the polymer backbone. In general, the fraction of ionized units can range from about 1 mole percent to about 90 mole percent. For example, in some embodiments, the content of ionized units is less than about 15 mole percent: and in other embodiments, the ionic content is higher, such as greater than about 80 mole percent. In still other embodiments, the ionic content is defined by an intermediate range, for example, in a range of about 15 to about 80 mole percent. Ionized repeating units in an ionomer can include anionic functional groups such as sulfonate, carboxylate, and the like. These functional groups can be charge balanced by, mono-, di-, or higher-valent cations, such as alkali or alkaline earth metals. Ionomers can also include polymer compositions containing attached or embedded quaternary ammonium, sulfonium, phosphazenium, and guanidinium residues or salts. Suitable examples will be familiar to one having ordinary skill in the art.

In some embodiments, polymers useful as a separator can include highly fluorinated or perfluorinated polymer backbones. Certain polymers useful in the present disclosure can include copolymers of tetrafluoroethylene and one or more fluorinated, acid-functional co-monomers, which are commercially available as NAFION™ perfluorinated polymer electrolytes from DuPont. Other useful perfluorinated polymers can include copolymers of tetrafluoroethylene and $FSO_2$—$CF_2CF_2CF_2CF_2$—O—CF=$CF_2$, FLEMION™ and SELEMION™.

Additionally, substantially non-fluorinated membranes that are modified with sulfonic acid groups (or cation exchanged sulfonate groups) can also be used. Such membranes can include those with substantially aromatic backbones such as, for example, polystyrene, polyphenylene, biphenyl sulfone (BPSH), or thermoplastics such as polyetherketones and polyethersulfones.

Battery-separator style porous membranes, can also be used as the separator. Because they contain no inherent ionic conduction capabilities, such membranes are typically impregnated with additives in order to function. These membranes typically contain a mixture of a polymer and inorganic filler, and open porosity. Suitable polymers can include, for example, high density polyethylene, polypropylene, polyvinylidene difluoride (PVDF), or polytetrafluoroethylene (PTFE). Suitable inorganic fillers can include silicon carbide matrix material, titanium dioxide, silicon dioxide, zinc phosphide, and ceria.

Separators can also be formed from polyesters, polyetherketones, poly(vinyl chloride), vinyl polymers, and substituted vinyl polymers. These can be used alone or in combination with any previously described polymer.

Porous separators are non-conductive membranes which allow charge transfer between two electrodes via open channels filled with electrolyte. The permeability increases the probability of chemicals (e.g., active materials) passing through the separator from one electrode to another and causing cross-contamination and/or reduction in cell energy efficiency. The degree of this cross-contamination can depend on, among other features, the size (the effective diameter and channel length), and character (hydrophobicity/hydrophilicity) of the pores, the nature of the electrolyte, and the degree of wetting between the pores and the electrolyte.

The pore size distribution of a porous separator is generally sufficient to substantially prevent the crossover of active materials between the two electrolyte solutions. Suitable porous membranes can have an average pore size distribution of between about 0.001 nm and 20 micrometers, more typically between about 0.001 nm and 100 nm. The size distribution of the pores in the porous membrane can be substantial. In other words, a porous membrane can contain a first plurality of pores with a very small diameter (approximately less than 1 nm) and a second plurality of pores with a very large diameter (approximately greater than 10 micrometers). The larger pore sizes can lead to a higher amount of active material crossover. The ability for a porous membrane to substantially prevent the crossover of active materials can depend on the relative difference in size between the average pore size and the active material. For example, when the active material is a metal center in a coordination complex, the average diameter of the coordination complex can be about 50% greater than the average pore size of the porous membrane. On the other hand, if a porous membrane has substantially uniform pore sizes, the average diameter of the coordination complex can be about 20% larger than the average pore size of the porous membrane. Likewise, the average diameter of a coordination complex is increased when it is further coordinated with at least one water molecule. The diameter of a coordination complex of at least one water molecule is generally considered to be the hydrodynamic diameter. In such embodiments, the hydrodynamic diameter is generally at least about 35% greater than the average pore size. When the average pore size is substantially uniform, the hydrodynamic radius can be about 10% greater than the average pore size.

In some embodiments, the separator can also include reinforcement materials for greater stability. Suitable reinforcement materials can include nylon, cotton, polyesters, crystalline silica, crystalline titania, amorphous silica, amorphous titania, rubber, asbestos, wood or any combination thereof.

Separators within the flow batteries of the present disclosure can have a membrane thickness of less than about 500 micrometers, or less than about 300 micrometers, or less than about 250 micrometers, or less than about 200 micrometers, or less than about 100 micrometers, or less than about 75 micrometers, or less than about 50 micrometers, or less than about 30 micrometers, or less than about 25 micrometers, or less than about 20 micrometers, or less than about 15 micrometers, or less than about 10 micrometers. Suitable separators can include those in which the flow battery is capable of operating with a current efficiency of greater than about 85% with a current density of 100 mA/cm$^2$ when the separator has a thickness of 100 micrometers. In further embodiments, the flow battery is capable of operating at a current efficiency of greater than 99.5% when the separator has a thickness of less than about 50 micrometers, a current efficiency of greater than 99% when the separator has a thickness of less than about 25 micrometers, and a current efficiency of greater than 98% when the separator has a thickness of less than about 10 micrometers. Accordingly, suitable separators include those in which the flow battery is capable of operating at a voltage efficiency of greater than 60% with a current density of 100 mA/cm². In further embodiments, suitable separators can include those in which the flow battery is capable of operating at a voltage efficiency of greater than 70%, greater than 80% or even greater than 90%.

The diffusion rate of the first and second active materials through the separator can be less than about $1\times10^{-5}$ mol cm$^{-2}$ day$^{-1}$, or less than about $1\times10^{-6}$ mol cm$^{-2}$ day$^{-1}$, or less than about $1\times10^{-7}$ mol cm$^{-2}$ day$^{-1}$, or less than about $1\times10^{-9}$ mol cm$^{-2}$ day$^{-1}$, or less than about $1\times10^{-11}$ mol cm$^{-2}$ day$^{-1}$, or less than about $1\times10^{-13}$ mol cm$^{-2}$ day$^{-1}$, or less than about $1\times10^{-15}$ mol cm$^{-2}$ day$^{-1}$.

The flow batteries can also include an external electrical circuit in electrical communication with the first and second electrodes. The circuit can charge and discharge the flow battery during operation. Reference to the sign of the net ionic charge of the first, second, or both active materials relates to the sign of the net ionic charge in both oxidized and reduced forms of the redox active materials under the conditions of the operating flow battery. Further exemplary embodiments of a flow battery provide that (a) the first active material has an associated net positive or negative charge and is capable of providing an oxidized or reduced form over an electric potential in a range of the negative operating potential of the system, such that the resulting oxidized or reduced form of the first active material has the same charge sign (positive or negative) as the first active material and the ionomer membrane also has a net ionic charge of the same sign: and (b) the second active material has an associated net positive or negative charge and is capable of providing an oxidized or reduced form over an electric potential in a range of the positive operating potential of the system, such that the resulting oxidized or reduced form of the second active material has the same charge sign (positive or negative sign) as the second active material and the ionomer membrane also has a net ionic charge of the same sign; or both (a) and (b). In some embodiments, the net ionic charge in both the oxidized and reduced forms can be negative. The matching charges of the first and/or second active materials and the ionomer membrane can provide a high selectivity. More specifically, charge matching can provide less than about 3%, less than about 2%, less than about 1%, less than about 0.5%, less than about 0.2%, or less than about 0.1% of the molar flux of ions passing through the ionomer membrane as being attributable to the first or second active material. The term "molar flux of ions" will refer to the amount of ions passing through the ionomer membrane, balancing the charge associated with the flow of external electricity/electrons. That is, the flow battery is capable of operating or operates with the substantial exclusion of the active materials by the ionomer membrane, and such exclusion can be promoted through charge matching.

Flow batteries incorporating the electrolyte solutions of the present disclosure can have one or more of the following operating characteristics: (a) where, during the operation of the flow battery, the first or second active materials comprise less than about 3% of the molar flux of ions passing through the ionomer membrane; (b) where the round trip current efficiency is greater than about 70%, greater than about 80%, or greater than about 90%; (c) where the round trip current efficiency is greater than about 90%; (d) where the sign of the net ionic charge of the first, second, or both active materials is the same in both oxidized and reduced forms of the active materials and matches that of the ionomer membrane; (e) where the ionomer membrane has a thickness of less than about 100 µm, less than about 75 µm, less than about 50 µm, or less than about 250 µm; (f) where the flow battery is capable of operating at a current density of greater than about 100 mA/cm² with a round trip voltage efficiency of greater than about 60%; and (g) where the energy density of the electrolyte solutions is greater than about 10 Wh/L, greater than about 20 Wh/L, or greater than about 30 Wh/L.

In some cases, a user may desire to provide higher charge or discharge voltages than available from a single battery cell. In such cases, several battery cells can be connected in series such that the voltage of each cell is additive. This forms a bipolar stack. An electrically conductive, but non-porous material (e.g., a bipolar plate) can be employed to connect adjacent battery cells in a bipolar stack, which allows for electron transport but prevents fluid or gas transport between adjacent cells. The positive electrode compartments and negative electrode compartments of individual cells can be fluidically connected via common positive and negative fluid manifolds in the stack. In this way, individual cells can be stacked in series to yield a voltage appropriate for DC applications or conversion to AC applications.

In additional embodiments, the cells, cell stacks, or batteries can be incorporated into larger energy storage systems, suitably including piping and controls useful for operation of these large units. Piping, control, and other equipment suitable for such systems are known in the art, and can include, for example, piping and pumps in fluid communication with the respective chambers for moving electrolyte solutions into and out of the respective chambers and storage tanks for holding charged and discharged electrolytes. The cells, cell stacks, and batteries of this disclosure can also include an operation management system. The operation management system can be any suitable controller device, such as a computer or microprocessor, and can contain logic circuitry that sets operation of any of the various valves, pumps, circulation loops, and the like.

In more specific embodiments, a flow battery system can include a flow battery (including a cell or cell stack); storage tanks and piping for containing and transporting the electrolyte solutions; control hardware and software (which may include safety systems); and a power conditioning unit. The flow battery cell stack accomplishes the conversion of charging and discharging cycles and determines the peak power. The storage tanks contain the positive and negative active materials, such as the coordination complexes disclosed herein, and the tank volume determines the quantity of energy stored in the system. The control software, hardware, and optional safety systems suitably include sensors, mitigation equipment and other electronic/hardware controls and safeguards to ensure safe, autonomous, and efficient operation of the flow battery system. A power conditioning unit can be used at the front end of the energy storage system to convert incoming and outgoing power to a voltage and current that is optimal for the energy storage system or the application. For the example of an energy storage system connected to an electrical grid, in a charging cycle the power conditioning unit can convert incoming AC electricity into DC electricity at an appropriate voltage and current for the cell stack. In a discharging cycle, the stack produces DC electrical power and the power conditioning unit converts it to AC electrical power at the appropriate voltage and frequency for grid applications.

Where not otherwise defined hereinabove or understood by one having ordinary skill in the art, the definitions in the following paragraphs will be applicable to the present disclosure.

As used herein, the term "energy density" will refer to the amount of energy that can be stored, per unit volume, in the active materials. Energy density refers to the theoretical energy density of energy storage and can be calculated by Equation 1:

$$\text{Energy density} = (26.8 \text{ A-h/mol}) \times OCV \times [e^-] \quad (1)$$

where OCV is the open circuit potential at 50% state of charge, (26.8 A-h/mol) is Faraday's constant, and $[e^-]$ is the concentration of electrons stored in the active material at 99% state of charge. In the case that the active materials largely are an atomic or molecular species for both the positive and negative electrolyte, $[e^-]$ can be calculated by Equation 2 as:

$$[e^-] = [\text{active materials}] \times N/2 \quad (2)$$

where [active materials] is the molar concentration of the active material in either the negative or positive electrolyte, whichever is lower, and N is the number of electrons transferred per molecule of active material. The related term "charge density" will refer to the total amount of charge that each electrolyte contains. For a given electrolyte, the charge density can be calculated by Equation 3

$$\text{Charge density} = (26.8 \text{ A-h/mol}) \times [\text{active material}] \times N \quad (3)$$

where [active material] and N are as defined above.

As used herein, the term "current density" will refer to the total current passed in an electrochemical cell divided by the geometric area of the electrodes of the cell and is commonly reported in units of $mA/cm^2$.

As used herein, the term "current efficiency" ($I_{eff}$) can be described as the ratio of the total charge produced upon discharge of a cell to the total charge passed during charging. The current efficiency can be a function of the state of charge of the flow battery. In some non-limiting embodiments, the current efficiency can be evaluated over a state of charge range of about 35% to about 60%.

As used herein, the term "voltage efficiency" can be described as the ratio of the observed electrode potential, at a given current density, to the half-cell potential for that electrode (×100%). Voltage efficiencies can be described for a battery charging step, a discharging step, or a "round trip voltage efficiency." The round trip voltage efficiency ($V_{eff,rt}$) at a given current density can be calculated from the cell voltage at discharge ($V_{discharge}$) and the voltage at charge ($V_{charge}$) using equation 4:

$$V_{eff,RT} = V_{discharge}/V_{charge} \times 100\% \quad (4)$$

As used herein, the terms "negative electrode" and "positive electrode" are electrodes defined with respect to one another, such that the negative electrode operates or is designed or intended to operate at a potential more negative than the positive electrode (and vice versa), independent of the actual potentials at which they operate, in both charging and discharging cycles. The negative electrode may or may not actually operate or be designed or intended to operate at a negative potential relative to a reversible hydrogen electrode. The negative electrode is associated with a first electrolyte solution and the positive electrode is associated with a second electrolyte solution, as described herein. The electrolyte solutions associated with the negative and positive electrodes may be described as negolytes and posolytes, respectively.

EXAMPLES

Standard laboratory procedures intended to exclude ambient atmosphere were followed in the syntheses described herein.

Example 1

Synthesis of NaKTi(catechol)$_3$. An oven-dried 5 L round-bottom flask was equipped with an overhead stirrer, condenser and septa. A moderate flow of nitrogen gas was then flowed through the system to purge the environment in the flask. The nitrogen outlet was placed at the top of the condenser and was connected to a base trap containing 150 g NaOH in 1 L of water.

To the flask was then added 600 mL of o-xylene, followed by 298.25 g (2.708 mol, 2.97 molar equivalents) of catechol. Stirring was started and an additional 100 mL of o-xylene was then added. The mixture was then heated until the catechol dissolved at a temperature of about 75° C.-80° C. The reaction was maintained at this temperature while adding TiCl$_4$.

In a separate flask, 100 mL of o-xylene was degassed by sparging with nitrogen gas. Into a tared, oven-dried 500 mL amber bottle fitted with a septum was transferred 173 g TiCl$_4$ (100 mL; 0.912 mol, 1.0 molar equivalents), and the degassed o-xylene was transferred to the amber bottle via a cannula. The TiCl$_4$ dissolved in the o-xylene to produce a dark solution. The TiCl$_4$ solution was then added dropwise via cannula to the heated catechol solution. Vigorous reaction occurred in some instances as the initial drops of the TiCl$_4$ solution were added. During the addition over about 2 hours, the reaction mixture turned dark red and then dark brown, and HCl was evolved from the reaction mixture. Solids formed in the reaction mixture during addition of the TiCl$_4$ solution.

After the addition of the TiCl$_4$ solution was complete, the temperature was raised to 120° C., and stirring was then maintained for 17 hours. The nitrogen flow was maintained at a rate sufficient to carry HCl vapors from the flask without substantially removing the o-xylenes solvent.

After the 17-hour heating period was complete, a check for HCl evolution at the nitrogen outlet was conducted with wet pH paper. As a second check that HCl evolution was complete, the nitrogen outlet tube was bubbled into a small quantity of deionized water, and the pH was checked to confirm that the water was non-acidic.

After confirming that HCl evolution was complete, an alkaline aqueous solution was added to the reaction mixture. Specifically, the alkaline aqueous solution was prepared by dissolving 35.57 g NaOH (0.889 mol, 0.975 molar equivalents) and 58.7 g KOH (0.889 mol, 0.975 molar equivalent) in 600 mL of deionized water, followed by degassing with nitrogen sparge for at least 1 hour. The alkaline aqueous solution was then added dropwise to the heated reaction via cannula over 1 hour. Stirring was maintained following the transfer, and the combined reaction mixture was then refluxed for a further three hours.

Following the 3-hour reflux, an aliquot of the resulting aqueous phase was withdrawn, and its pH was determined to be 7.52. A solution containing 4.33 g Na$_4$EDTA (0.0114 mol, 0.0125 molar equivalents), 5.04 g K$_3$EDTA (0.0114 mol, 0.0125 molar equivalents), 0.46 g NaOH (0.0114 mol, 0.0125 molar equivalents) and 1.51 g KOH (0.0228 mol, 0.0250 molar equivalents) dissolved in 100 mL deionized water was then added dropwise over 1 hour to the reaction. The reaction mixture was refluxed for an additional hour, and an aliquot of the aqueous phase was again withdrawn. Following introduction of the additional bases, the pH of the aqueous phase was measured at 10.10.

The reaction mixture was then cooled to about 60° C. and filtered while hot through a coarse fritted glass funnel. The filtrate was then collected and re-filtered through a medium fritted glass funnel. The filtrate layers were then allowed to partition in a separatory funnel while cooling to room temperature. The lower aqueous phase was then collected and further analyses were conducted. The experimentally determined concentration for the alkali metal salt form titanium catechol complex was 0.87 M, providing a yield of 92%. Experimental data for the aqueous phase containing the complex will be presented below for a larger scale synthesis.

Example 2

Synthesis of NaKTi(catechol)$_3$ at a 72 L Scale. A 72 L roundbottom glass reactor was equipped with a mechanical stirrer, condenser, and 1 L addition funnel. A moderate flow of nitrogen gas (7 L/min) was then flowed through the system. The nitrogen outlet was connected to a base trap.

To the flask was then added 8.621 kg of catechol (78.290 mol, 2.95 molar equivalents) and 20 L of xylenes. Stirring was started, and an additional 5 L of xylenes was then added. The mixture was heated until the catechol dissolved at a temperature of about 75° C.-80° C. The reaction was then maintained at this temperature while adding TiCl$_4$.

To the addition funnel was added 5.041 kg of neat TiCl$_4$ (2.914 L; 26.576 mol, 1.00 molar equivalent) via a cannula. The TiCl$_4$ solution was then added dropwise to the heated catechol solution at a rate of about 6 mL/min over about 8 hours. The reaction mixture was heated at 60° C. for 12 hours under nitrogen flow and then for a further 12 hours at 60° C. at a pressure of 120 torr. The nitrogen purge was discontinued during the vacuum heating step. The base trap was titrated to determine the amount of HCl gas released, ensuring the amount was near theoretical levels (>99% of theoretical HCl released), and additional monitoring was conducted as above to ensure that HCl release was complete. After the vacuum heating step was completed, the nitrogen purge was resumed.

The reactor was then heated to 80° C. and placed under a flowing nitrogen purge. To the reaction mixture was then added 18.75 L of a 3 M alkaline aqueous solution containing equimolar amounts of NaOH and KOH (1.03 kg NaOH and 1.579 kg KOH, each 25.701 mol, 0.975 molar equivalents) over a 2.5-hour addition time. The NaOH/KOH solution was spared with nitrogen before use. The pH of the resulting aqueous phase was then adjusted by adding an additional 0.12 equivalents of NaOH and KOH to the reaction mixture (3 M solution of equimolar NaOH and KOH). Once a stable pH of 9-10 was attained, stirring was stopped to allow the phases to separate. The actual final pH of the aqueous phase was 9.87. The lower aqueous phase was siphoned from the reactor and hot filtered via centrifuge through an aqueous Celite 577 cake containing 262 grams of filtering agent. An emulsion in the residual organic phase in the reactor was also allowed to settle during this time, and additional centrifugation was conducted to obtain a further quantity of aqueous phase, which was combined with the initially separated aqueous phase.

Figure 2A:
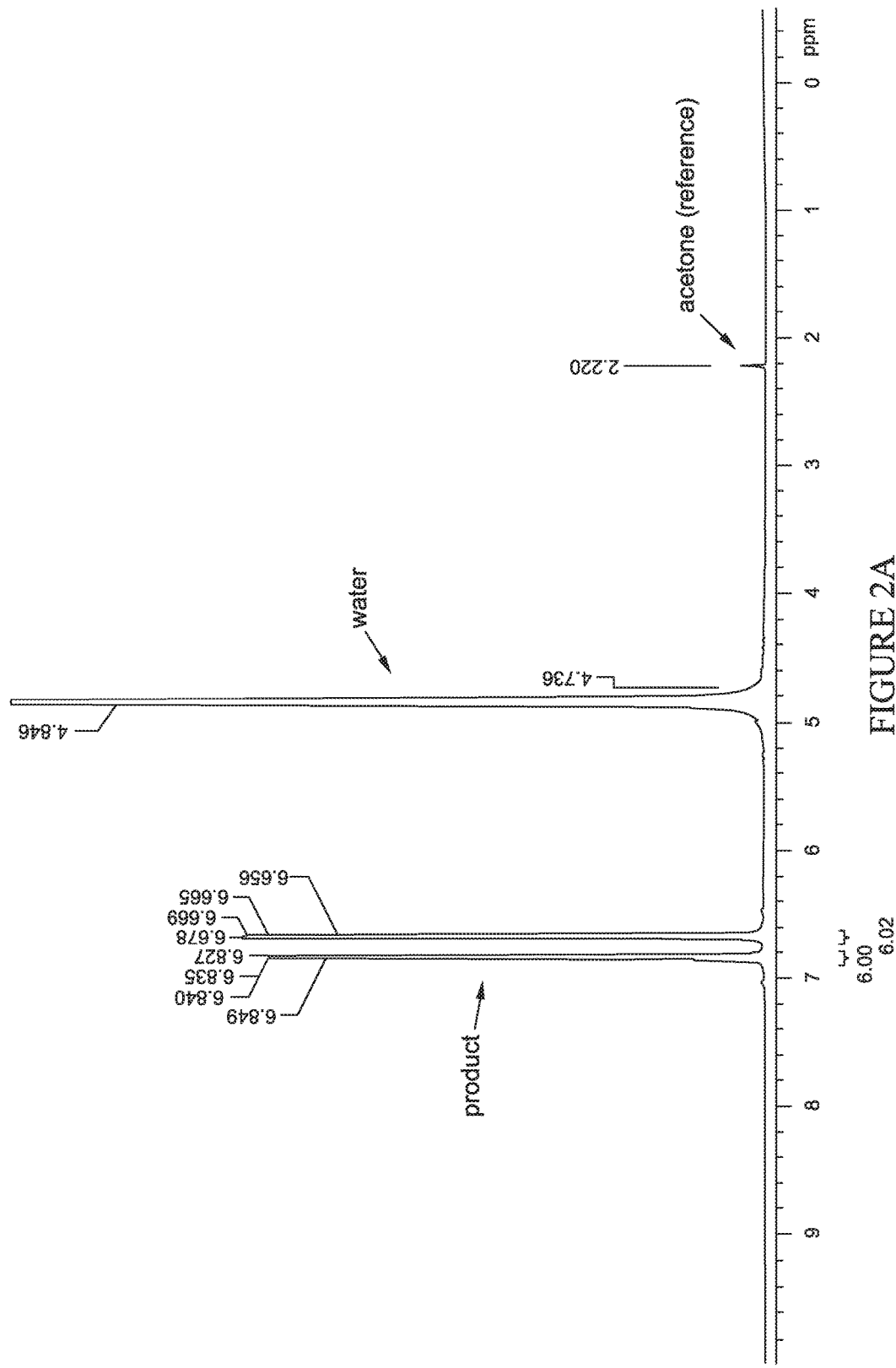
FIGS. 2A and 2B show illustrative $^1$H NMR spectra for the NaKTi(catechol)$_3$ complex in D$_2$O against an acetone reference.
Figure 2B:
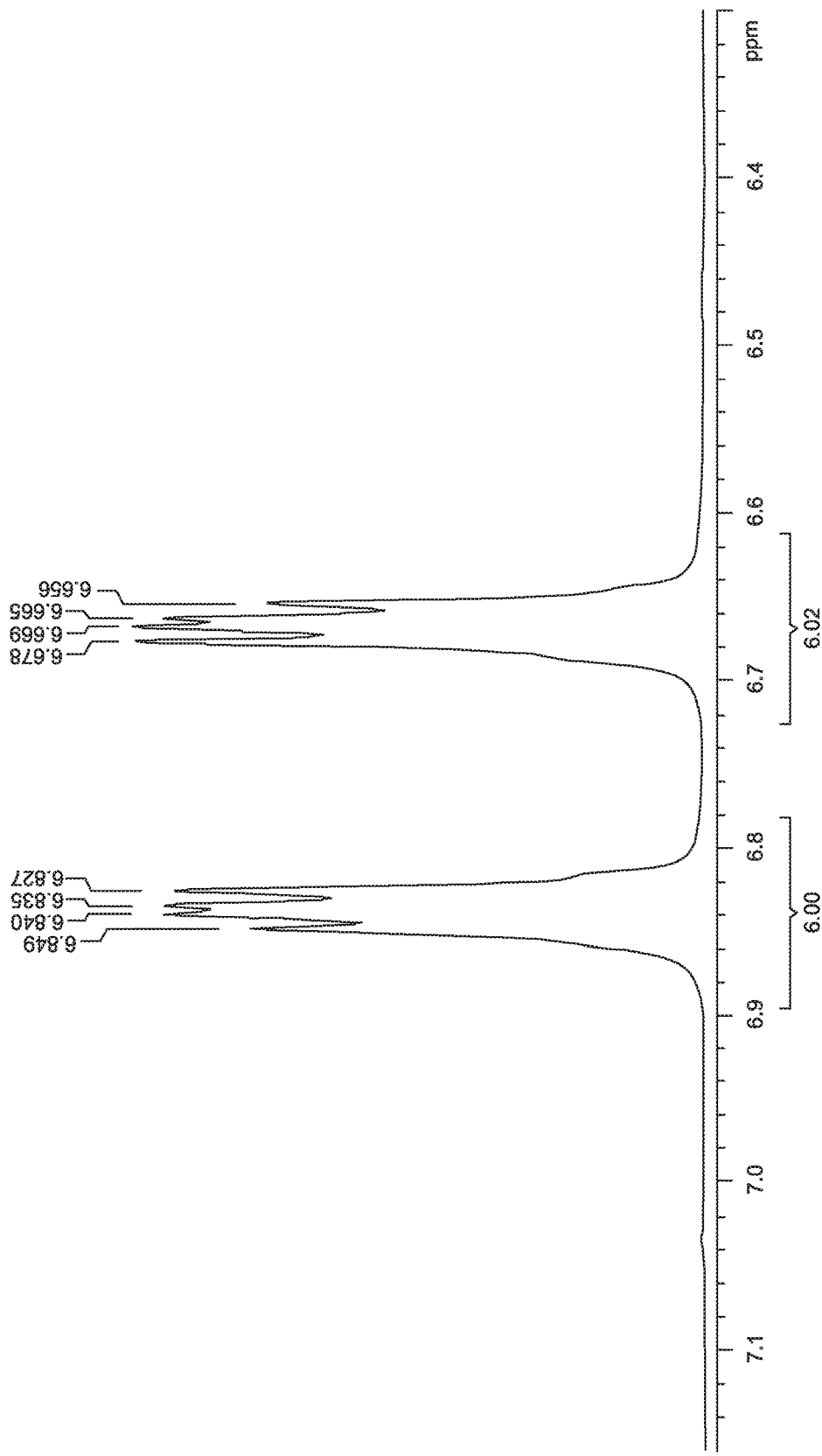
Figure 3A:
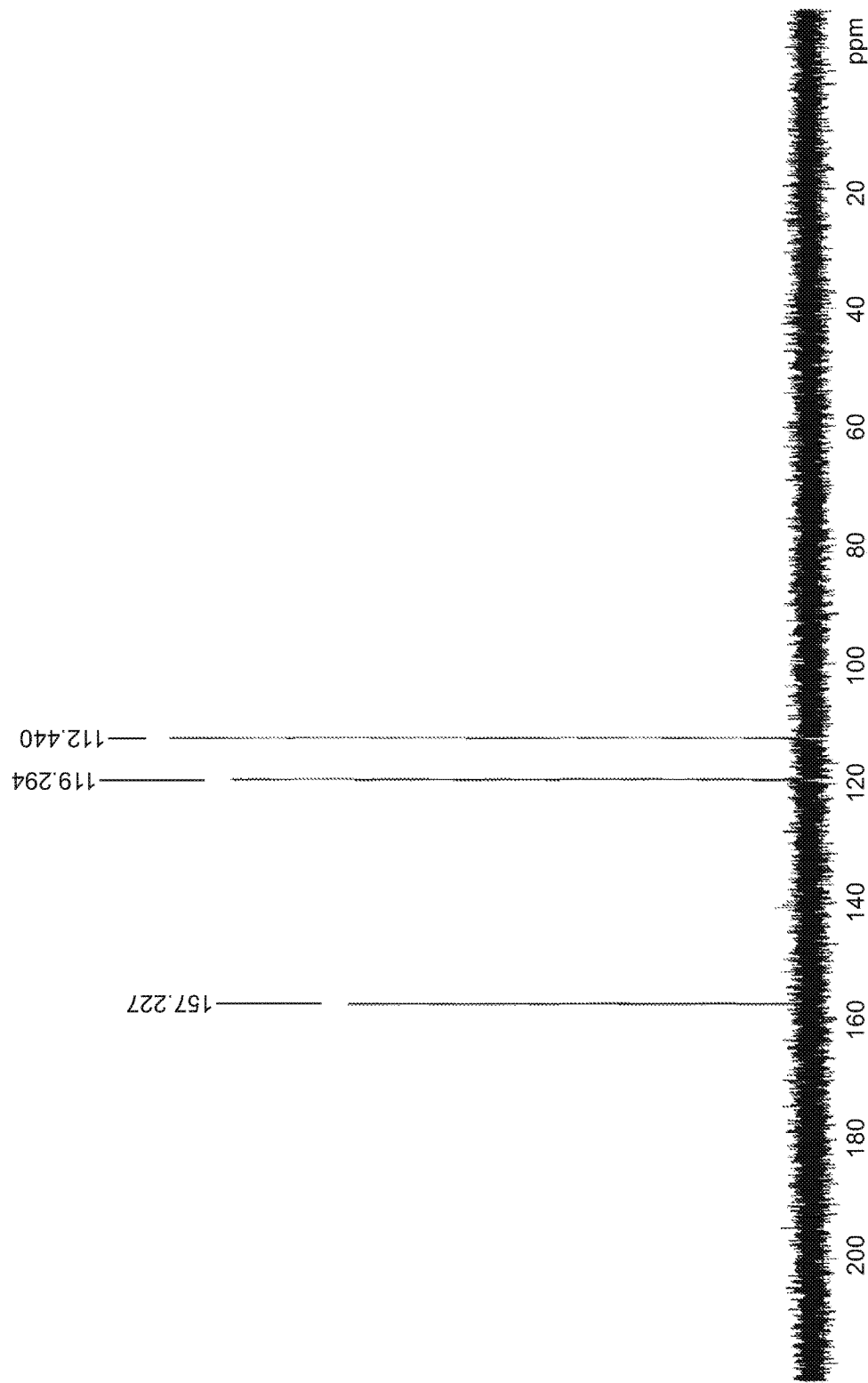
FIGS. 3A and 3B show illustrative $^{13}$C NMR spectra for the NaKTi(catechol)$_3$ complex in D$_2$O.
Figure 3B:
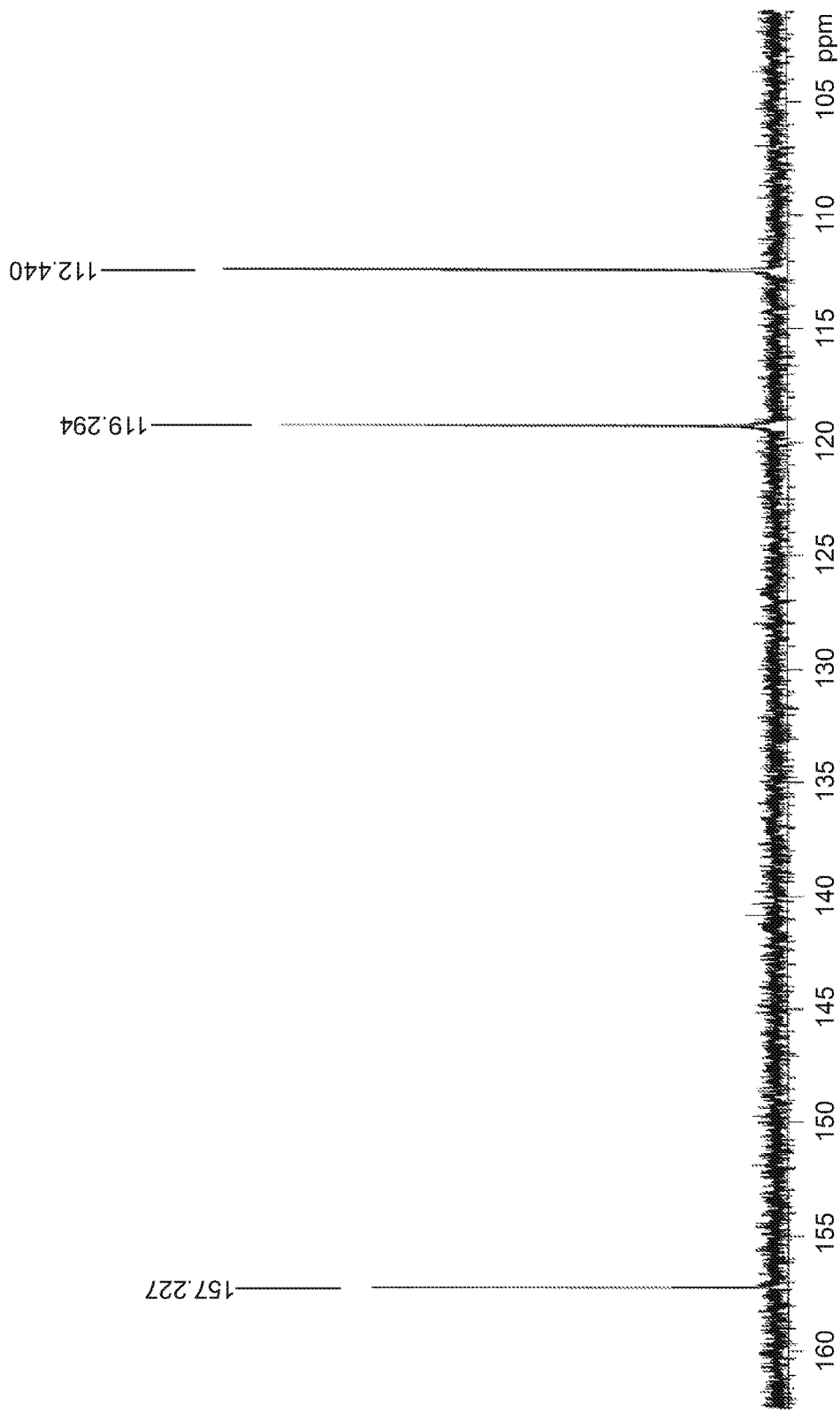
Figure 4:
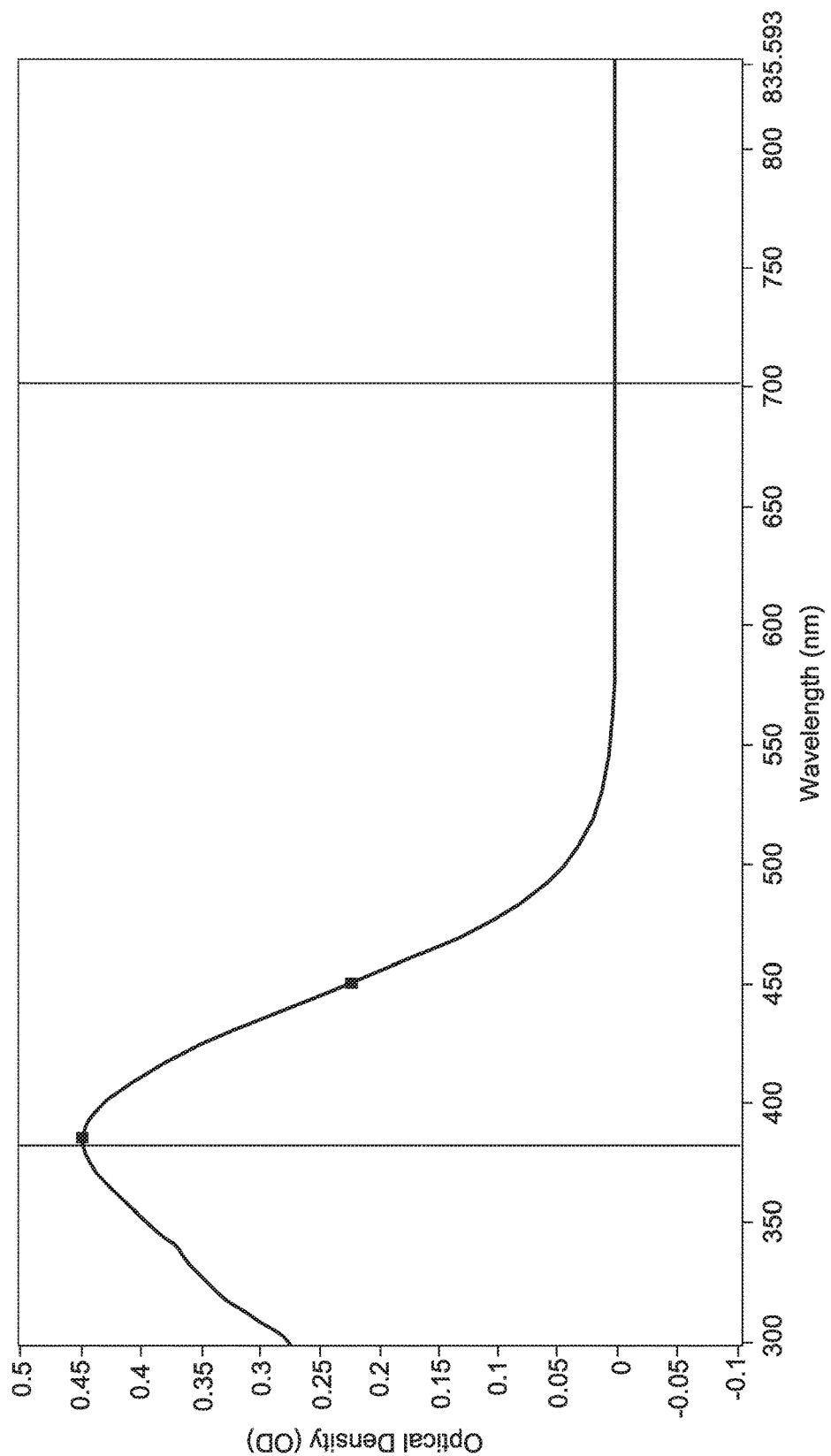
FIG. 4 shows an illustrative UV-VIS spectrum of the NaKTi(catechol)$_3$ complex in water.

The total volume of the aqueous phase collected following filtration was 25.5 L, and the concentration of the alkali metal salt form titanium catechol complex was measured at 0.84 M using UV-VIS spectroscopy. Based on the measured concentration and collected volume, the yield was 82%. Free catechol was undetectable by $^1$H NMR. The aqueous phase was dark red and clear following its isolation. FIGS. 2A and 2B show illustrative $^1$H NMR spectra for the NaKTi(catechol)$_3$ complex in D$_2$O against an acetone reference. FIGS. 3A and 3B show illustrative $^{13}$C NMR spectra for the NaKTi(catechol)$_3$ complex in D$_2$O. FIG. 4 shows an illustrative UV-VIS spectrum of the NaKTi(catechol)$_3$ complex in water.

Although the disclosure has been described with reference to the disclosed embodiments, those skilled in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description.

What is claimed is the following:

1. A method comprising:
   heating a catechol solution comprising a catechol compound and an organic solvent;
   adding titanium tetrachloride to the heating catechol solution to form a reaction mixture;
   reacting the titanium tetrachloride with the catechol compound to evolve HCl gas from the reaction mixture and to form an intermediate titanium catechol complex; and
   adding an alkaline aqueous solution to the intermediate titanium catechol complex, the alkaline aqueous solution comprising an alkali metal base;
   wherein the alkali metal base converts the intermediate titanium catechol complex into an alkali metal salt form titanium catechol complex that is at least partially dissolved in an aqueous phase.

2. The method of claim 1, wherein the catechol compound is 1,2-dihydroxybenzene.

3. The method of claim 1, wherein the catechol compound comprises at least one substituted catechol compound.

4. The method of claim 3, wherein the at least one substituted catechol compound comprises 3,4-dihydroxybenzenesulfonic acid.

5. The method of claim 1, wherein the alkali metal base comprises an alkali metal hydroxide selected from the group consisting of sodium hydroxide, potassium hydroxide, and any combination thereof.

6. The method of claim 1, wherein the alkali metal base comprises a mixture of sodium hydroxide and potassium hydroxide.

7. The method of claim 1, wherein the HCl gas is substantially removed from the reaction mixture before adding the alkaline aqueous solution to the intermediate titanium catechol complex.

8. The method of claim 7, wherein the reaction mixture is maintained at a reduced pressure before adding the alkaline aqueous solution thereto.

9. The method of claim 7, wherein a flowing inert gas contacts the reaction mixture while evolving the HCl gas therefrom.

10. The method of claim 1, wherein the intermediate titanium catechol complex is insoluble in the reaction mixture.

11. The method of claim 1, wherein the intermediate titanium catechol complex is not isolated from the reaction mixture before adding the alkaline aqueous solution thereto.

12. The method of claim 1, wherein the organic solvent comprises a water-immiscible organic solvent.

13. The method of claim 12, wherein the water-immiscible organic solvent is selected from the group consisting of toluene, xylenes, cyclohexane, dichloromethane, dichloroethane, and any combination thereof.

14. The method of claim 1, wherein an amount of the alkali metal base in the alkaline aqueous solution is such that the aqueous phase containing the alkali metal salt form titanium catechol complex has a pH of about 6 to about 8.

15. The method of claim 14, further comprising:
adding an additional quantity of the alkaline aqueous solution or a different alkaline aqueous solution to the aqueous phase to adjust the pH of the aqueous phase to a range of about 9 to about 10.

16. The method of claim 1, wherein the alkali metal salt form titanium catechol complex has a formula of

$D_2Ti(L)_3$;

wherein D is an alkali metal ion or a mixture of alkali metal ions, and L is a substituted catecholate ligand, an unsubstituted catecholate ligand, or any combination thereof.

17. The method of claim 1, wherein the intermediate titanium catechol complex and the alkali metal salt form titanium catechol complex are formed consecutively in a single reaction vessel.

18. The method of claim 1 comprising:
heating a catechol solution comprising a catechol compound and an organic solvent, the organic solvent being water-immiscible;
while heating the catechol solution, adding titanium tetrachloride thereto to evolve HCl gas and to form a reaction mixture comprising an intermediate titanium catechol complex, wherein the intermediate titanium catechol complex is insoluble in the reaction mixture;
without isolating the intermediate titanium catechol complex from the reaction mixture, adding an alkaline aqueous solution to the intermediate titanium catechol complex;
wherein the alkaline aqueous solution comprises an alkali metal base;
reacting the alkali metal base with the intermediate titanium catechol complex to form an alkali metal salt form titanium catechol complex that is at least partially dissolved in an aqueous phase; and
separating the aqueous phase and an organic phase from one another.

19. The method of claim 18, wherein the alkali metal base comprises a mixture of sodium hydroxide and potassium hydroxide.

20. The method of claim 18, wherein heating is continued after adding the alkaline aqueous solution to the reaction mixture.

21. The method of claim 18, wherein the HCl gas is substantially removed from the reaction mixture before adding the alkaline aqueous solution thereto.

22. The method of claim 21, wherein the reaction mixture is maintained at a reduced pressure before adding the alkaline aqueous solution thereto.

23. The method of claim 21, wherein a flowing inert gas contacts the reaction mixture while evolving the HCl gas therefrom.

24. The method of claim 18, wherein an amount of the alkali metal base in the alkaline aqueous solution is such that the aqueous phase containing the alkali metal salt form titanium catechol complex has a pH of about 6 to about 8.

25. The method of claim 24, further comprising:
adding an additional quantity of the alkaline aqueous solution or a different alkaline aqueous solution to the aqueous phase to adjust the pH of the aqueous phase to a range of about 9 to about 10.

* * * * *

UNITED STATES PATENT AND TRADEMARK OFFICE
CERTIFICATE OF CORRECTION

PATENT NO. : 10,343,964 B2
APPLICATION NO. : 15/220322
DATED : July 9, 2019
INVENTOR(S) : Matthew Millard It is certified that error appears in the above-identified patent and that said Letters Patent is hereby corrected as shown below:

On the Title Page

Item [56], References Cited, Under heading FOREIGN PATENT DOCUMENTS, Line 7:
Replace "153366" with --1533662--

Item [56], References Cited, Under heading OTHER PUBLICATIONS:
Replace "Davies, "Electroceramics from Source Materials via Molecular Intermediates: BaTI03 from TI02 via [TI (catecholate)3]2-," May 1990, J. Am. Ceram, Soc., Aug. 1990, 73(5), 1429-30." with --Davies, "Electroceramics from Source Materials via Molecular Intermediates: BaTiO3 from TiO2 via [Ti (catecholate)3]2-," May 1990, J. Am. Ceram, Soc., Aug. 1990, 73(5), 1429-30.--

Replace "Davies, "Electroceramics from Source Materials via Molecular Intermediates: PbTi03 from Ti02 via [Ti (catecholate)3]2-," J. Am. Ceram. Soc., Aug. 1990, 73(8), 2570-2572." with --Davies, "Electroceramics from Source Materials via Molecular Intermediates: PbTiO3 from TiO2 via [Ti (catecholate)3]2-," J. Am. Ceram. Soc., Aug. 1990, 73(8), 2570-2572.--

Replace "Raymond , "Coordination isomers of biological iron transport compounds. VI. Models of the enterobactin coordination site. A crystal field effect in the structure of potassium tris( catecholato)chromate( III) and -ferrate ( III) sesq u ihyd rates, K3[M( 02C6H4)3]. 1 . 5H20, M=chromium, iron," J. Am. Chem. Soc., Mar. 1976, 98(7), 1767-1774." with --Raymond , "Coordination isomers of biological iron transport compounds. VI. Models of the enterobactin coordination site. A crystal field effect in the structure of potassium tris( catecholato)chromate( III) and -ferrate ( III) sesquihydrates, K3[M(O2C6H4)3].cntdot.1.5H2O, M = chromium, iron," J. Am. Chem. Soc., Mar. 1976, 98 (7), 1767-1774.--

Replace "Saito et al. "DPPH radical-scavenging reaction of protocatechuic acid: differnce in reactivity between acids and their esters," Hely Chim Acta, 2006, pp. 1395-1407, vol. 89." with --Saito et al. "DPPH radical-scavenging reaction of protocatechuic acid: difference in reactivity between acids and their esters," Hely Chim Acta, 2006, pp. 1395-1407, vol. 89.--

Signed and Sealed this
Twenty-fourth Day of March, 2020

Andrei Iancu
*Director of the United States Patent and Trademark Office*

Replace "Sommer, "Titanium (IV) complexes with ligands having oxygen donor atoms in aqueous solutions," Zeitschrift fur Anorganische and Aligemeine Chemie, Mar. 1963, pp. 191-197, vol. 321, issue 3-4." with --Sommer, "Titanium (IV) complexes with ligands having oxygen donor atoms in aqueous solutions," Zeitschrift fur Anorganische und Aligemeine Chemie, Mar. 1963, pp. 191-197, vol. 321, issue 3-4.--